(12) United States Patent
Rotfogel et al.

(10) Patent No.: US 11,791,657 B2
(45) Date of Patent: Oct. 17, 2023

(54) APPARATUS FOR HARVESTING ENERGY FROM RELATIVE MOTION OF BODY PARTS, PARTICULARLY AN EYEBALL AND AN EYELID

(71) Applicant: MOR RESEARCH APPLICATIONS LTD., Tel Aviv (IL)

(72) Inventors: Ziv Rotfogel, Kfar Saba (IL); Nadav Cohen, Misgav (IL)

(73) Assignee: BLINK ENERGY LTD., Haifa (IL)

( * ) Notice: Subject to any disclaimer, the term of this patent is extended or adjusted under 35 U.S.C. 154(b) by 576 days.

(21) Appl. No.: 17/055,588

(22) PCT Filed: May 13, 2019

(86) PCT No.: PCT/IB2019/053929
§ 371 (c)(1),
(2) Date: Nov. 15, 2020

(87) PCT Pub. No.: WO2019/220307
PCT Pub. Date: Nov. 21, 2019

(65) Prior Publication Data
US 2021/0226476 A1    Jul. 22, 2021

Related U.S. Application Data

(60) Provisional application No. 62/670,933, filed on May 14, 2018.

(51) Int. Cl.
*A61F 2/16* (2006.01)
*H02J 50/00* (2016.01)
(Continued)

(52) U.S. Cl.
CPC .............. *H02J 50/001* (2020.01); *A61F 2/16* (2013.01); *G02C 7/04* (2013.01); *G02C 11/10* (2013.01);
(Continued)

(58) Field of Classification Search
CPC .......... H02J 50/001; H02J 7/007; H02J 50/10; H02J 2207/20; A61F 2/16; G02C 7/04; G02C 11/10
See application file for complete search history.

(56) References Cited

U.S. PATENT DOCUMENTS 11,624,938 B2 * 4/2023 Miller .................... G03B 21/14
455/41.1
11,662,807 B2 * 5/2023 Haine ...................... G02C 7/04
345/633

(Continued)

*Primary Examiner* — Suzette J Gherbi
(74) *Attorney, Agent, or Firm* — Mark M. Friedman

(57) ABSTRACT

A system for providing electrical energy to an implanted device or to a device attached to a body. The system includes one or more permanent magnets attached to or implanted in a first body part and one or more inductor(s) attached to or implanted in a second body part. The inductor(s) are electrically couplable to the implanted device for providing the implanted device with electrical currents flowing in the one or more inductor(s) in response to changes in the position and/or orientation of the permanent magnet(s) relative to the position and/or orientation of the inductor(s). The system may include a current rectifier for rectifying electrical currents provided by the inductor(s). The system may also include a charge storage device electrically coupled to the current rectifier for storing electrical energy received from the current rectifier.

20 Claims, 10 Drawing Sheets

(51) Int. Cl.
*H02J 50/10* (2016.01)
*G02C 7/04* (2006.01)
*G02C 11/00* (2006.01)
*H02J 7/00* (2006.01)

(52) U.S. Cl.
CPC .............. *H02J 7/007* (2013.01); *H02J 50/10* (2016.02); *H02J 2207/20* (2020.01)

(56) References Cited

U.S. PATENT DOCUMENTS

| | | | |
|---|---|---|---|
| 11,681,160 B2* | 6/2023 | Hekmat | H01M 10/425 351/159.02 |
| 11,720,170 B2* | 8/2023 | Barbier | G01C 3/14 324/207.22 |
| 2018/0043646 A1* | 2/2018 | Lai | G02C 11/10 |

* cited by examiner

APPARATUS FOR HARVESTING ENERGY FROM RELATIVE MOTION OF BODY PARTS, PARTICULARLY AN EYEBALL AND AN EYELID

FIELD AND BACKGROUND

The present invention, in some embodiments thereof, relates to devices and systems for providing power to devices implanted in a body, particularly by harvesting energy from blinking motions. The field the devices or systems designed to be implanted in a body (whether a human body or the body of an animal, such as a body of a mammal, or of an invertebrate animal) is well known in the art. various different devices may be implanted in humans and/or animals for many different purposes, such as, for example, medical and/or therapeutic devices for delivering a medical or therapeutic treatment to a body, devices for delivering electrical stimulation to the body or to an organ of a body (such as cardiac pacemakers, cardiac defibrillators, and the like. Other such devices may include various types of implantable sensors for sensing and/or measuring and/or monitoring various physic-chemical parameters within the body. Such sensors may include, among others, temperature sensors, pressure sensors, acoustic sensors, sensors for sensing the concentration of a chemical species in the body, electrical conductivity sensors and the like.

Other implantable devices may be used to deliver a drug or pharmaceutical composition to the body (either locally or systemically) in a controlled manner.

A distinct class of implantable (medical or non-medical) devices are prostheses which may function to sense electrical activity in and/or to electrically stimulate neuronal tissues (such as, a region of the brain, a retina, a nerve or other neural tissues). Such devices may include brain computer interfaces (BCIs) to be implanted intra-cranially. Retinal implants implantable in an eye for substituting for a damaged or non-functioning retina). Various different types of cortical and deep brain electrode arrays are known in the art for stimulating nervous tissues and for sensing and/or recording neuronal associated electrical and optical activity.

A common problem with such implantable devices is that they often may require a substantial amount of power (typically electrical power) for their operation.

SUMMARY

There is therefore provided, in accordance with some embodiments, an energy harvesting apparatus for harvesting energy from relative motion of an eyeball and an eyelid to drive an electrical device, the energy harvesting apparatus, comprising: a coil of conductive wire; a support arrangement for supporting the coil in or on an eyeball; a permanent magnet configured for deployment in or on an eyelid, the permanent magnet generating a magnetic field oriented to generate a variation of magnetic flux through the coil on blinking motion of the eyelid; and rectifying circuitry electrically connected across the coil and configured to rectify an electrical output of the coil to generate a DC output for driving the electrical device.

According to a further feature of an embodiment of the present invention, there is also provided an electrical storage component electrically connected to the rectifying circuitry for storing energy from the DC output for driving the electrical device.

According to a further feature of an embodiment of the present invention, the support arrangement is configured to be applied to an external surface of the eyeball.

According to a further feature of an embodiment of the present invention, the support arrangement is integrated with a contact lens configured to be applied to an external surface of the eyeball.

According to a further feature of an embodiment of the present invention, the support arrangement is configured to be deployed intraoculary, optionally integrated with an intraocular lens.

According to a further feature of an embodiment of the present invention, the support arrangement is configured to support the coil with the coil encircling an optic axis of the eyeball.

According to a further feature of an embodiment of the present invention, there is also provided a soft magnetic core mechanically associated with, and deployed within, the coil.

According to a further feature of an embodiment of the present invention, the permanent magnet is formed as a flat or curved slab contiguous in two major dimensions, and having a maximum local thickness, each of the two major dimensions being at least five times greater than the maximum local thickness.

According to a further feature of an embodiment of the present invention, a direction of magnetization of at least part of the permanent magnet is substantially perpendicular to both of the two major dimensions.

According to a further feature of an embodiment of the present invention, the permanent magnet is formed as a slab having a concave major surface for accommodating a curvature of the eyeball, and a convex major surface.

According to a further feature of an embodiment of the present invention, there is also provided a shield of soft-magnetic material deployed on an outward-facing surface of the permanent magnet.

According to a further feature of an embodiment of the present invention, the permanent magnet is implemented as a compound permanent magnet having a plurality of different regions of magnetization, the regions of magnetization having differing directions of magnetization so as to generate magnetic field shaping with enhanced flux intensity along an inwards-facing direction from the compound permanent magnet.

According to a further feature of an embodiment of the present invention, there is also provided an adhesive pad associated with the permanent magnet for attaching the permanent magnet to a surface of the eyelid.

According to a further feature of an embodiment of the present invention, the permanent magnet is encased in a non-magnetic layer of biocompatible material for implantation into the eyelid.

According to a further feature of an embodiment of the present invention, there is also provided voltage boosting circuitry electrically associated with the coil or the rectifying circuitry and configured to boost a voltage of the output reaching the electrical storage component.

There is also provided according to the teachings of an embodiment of the present invention, an energy harvesting apparatus for harvesting energy from relative motion of an eyeball and an eyelid to drive an electrical device, the energy harvesting apparatus, comprising: a coil of conductive wire deployed in or on the eyeball; a permanent magnet deployed in or on the eyelid, the permanent magnet generating a magnetic field oriented to generate a variation of magnetic flux through the coil on blinking motion of the eyelid; and rectifying circuitry electrically connected across the coil and configured to rectify an electrical output of the coil to generate a DC output for driving the electrical device.

According to a further feature of an embodiment of the present invention, there is also provided an electrical storage component electrically connected to the rectifying circuitry for storing energy from the DC output for driving the electrical device.

According to a further feature of an embodiment of the present invention, the coil is deployed on an external surface of the eyeball.

According to a further feature of an embodiment of the present invention, the coil is integrated with a contact lens applied to an external surface of the eyeball.

According to a further feature of an embodiment of the present invention, the coil is deployed in or under the conjunctiva or the sclera of the eyeball.

According to a further feature of an embodiment of the present invention, the coil is deployed in, or attached to, the cornea of the eyeball.

According to a further feature of an embodiment of the present invention, the coil is deployed within the vitreous body, the anterior chamber, the sulcus, the capsular bag or the posterior chamber of the eyeball.

According to a further feature of an embodiment of the present invention, the coil is integrated with an intraocular lens.

According to a further feature of an embodiment of the present invention, the coil is deployed encircling an optic axis of the eyeball.

According to a further feature of an embodiment of the present invention, there is also provided a soft magnetic core mechanically associated with, and deployed within, the coil.

According to a further feature of an embodiment of the present invention, the permanent magnet is formed as a flat or curved slab contiguous in two major dimensions, and having a maximum local thickness, each of the two major dimensions being at least five times greater than the maximum local thickness.

According to a further feature of an embodiment of the present invention, a direction of magnetization of at least part of the permanent magnet is substantially perpendicular to both of the two major dimensions.

According to a further feature of an embodiment of the present invention, the permanent magnet is formed as a slab having a concave major surface for accommodating a curvature of the eyeball, and a convex major surface.

According to a further feature of an embodiment of the present invention, there is also provided a shield of soft-magnetic material deployed on an outward-facing surface of the permanent magnet.

According to a further feature of an embodiment of the present invention, the permanent magnet is implemented as a compound permanent magnet having a plurality of different regions of magnetization, the regions of magnetization having differing directions of magnetization so as to generate magnetic field shaping with enhanced flux intensity along an inwards-facing direction from the compound permanent magnet.

According to a further feature of an embodiment of the present invention, the permanent magnet is attached to a surface of the eyelid.

According to a further feature of an embodiment of the present invention, the permanent magnet is implanted within the eyelid.

According to a further feature of an embodiment of the present invention, there is also provided voltage boosting circuitry electrically associated with the coil or the rectifying circuitry and configured to boost a voltage of the output reaching the electrical storage component.

BRIEF DESCRIPTION OF THE SEVERAL VIEWS OF THE DRAWINGS

Some embodiments are herein described, by way of example only, with reference to the accompanying drawings, in which like components are designated by like reference numerals. With specific reference now to the drawings in detail, it is stressed that the particulars shown are by way of example and for purposes of illustrative discussion of embodiments.

In the drawings.

DETAILED DESCRIPTION

Abbreviations

The following abbreviations are used throughout the specification and the claims of the present application:
AC—Alternating current
DC—Direct Current
EMF—Electro motive force
IC—Integrated Circuit
IOL—Intraocular Lens
mT—milli Tesla
m—meter
mm—millimeter
mWb/m—milliWeber per meter
μWb—micro Weber
PMMA—Polymethylmetacrylate
S/m—Siemens per meter
T—Tesla
Wb/m—Weber per meter
Ω—Ohm
VEGF—Vascular Endothelial Growth Factor
μW—Microwatt ($10^{-6}$ Watt)

The present application concerns systems and methods for using mechanical energy from movements of body parts to provide electrical power to devices implanted within a body of a living organism, such as a mammal.

Figure 1:
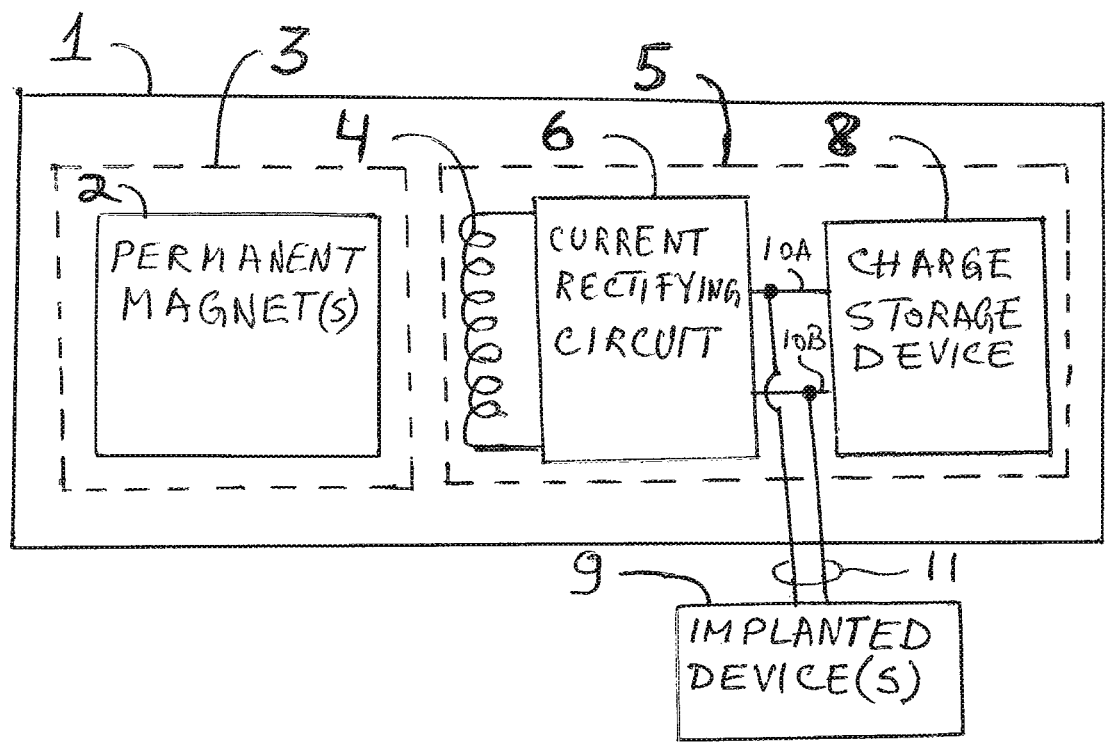
FIG. 1 is a schematic block diagram illustrating the components of a system for providing electrical energy to an implanted device.

Reference is now made to FIG. 1 which is a schematic block diagram illustrating the components of a system for providing electrical energy to an implanted device. The system 1 includes one or more permanent magnets 2 which is/are attached to or implanted within a first body part 3 (for example, an eyelid) and one or more electrically conducting inductor(s) 4 (such as, for example, one or more electrically conducting coils) which is/are attached to or implanted in a second body part 5. The second body part 5 is adjacent to and/or coupled to the first body part 3. For example, the inductor(s) 4 may be attached to an artificial lens implanted within the eye or coupled to the eye by a suitable contact lens or implanted within the eye. The inductor(s) 4 may be suitably electrically coupled (preferably, with suitable impedance matching) to current rectifying circuitry 6 for rectifying the currents flowing (in alternating directions) in the inductor(s) 4 into (pulsatile or) direct current (DC).

Some embodiments of the system preferably include an electrical charge storage device 8 (such as, for example, a rechargeable battery, a super capacitor, a capacitor, or any other device suitable for storing and retrieving electrical energy).

The operation of the system 1 is based on changes in the intensity of the to magnetic flux gradient within the inductor(s) 4 that result from movements (i.e., change in the position and/or orientation) of the permanent magnet(s) 2 relative to the inductor(s) 4. The charging power is proportional to the square of the time derivative of the magnetic flux. Such relative movements occur as a result of the movement of the first body part 2 relative to the second body part 5 or due to the movement of the second body part 5 relative to the first body part 3 or due to movement of both of the first body part 3 and the second body part 5. The change in the position of the permanent magnet(s) 2 relative to the inductor(s) 4 may change the intensity of the magnetic flux within the inductor(s) 4 which results in flow of electrical current within the inductor(s) 4. Different changes in the position of the permanent magnet(s) 2 and the inductor(s) 4 relative to each other may result in currents with different (opposite) directions and magnitudes. In a typical case of repetitive body motions, the currents are typically pulsatile currents that flow in opposite directions within the inductor(s) 4.

The rectifying circuitry 6 may be any type of electrical and/or electronic circuit suitable for rectifying alternating currents (pulsatile or periodic) into direct current. For example, in certain particularly preferred implementations, the rectifying circuitry 6 are implemented as a four diode full rectifying circuit. Other types of full wave or half wave current rectifying circuitry may also be used to implement the rectifying circuitry or any other rectifying technology 6. In some embodiments of the system, the direct current may be supplied to an implanted device which needs to be powered (such as, for example, a pacemaker implanted in the body which has an integral charge storing device). For example, in a case where the power is to be supplied to an implanted pacemaker, the pacemaker may have an integrated charge storage device (such as a rechargeable battery or electrochemical cell, a capacitor or a super capacitor, or any other suitable charge storing device). In such embodiments, the implanted device (such as, for example a pacemaker) may be operably connected with the current rectifying circuitry 6 e.g., via output terminals 10A and 10B of by a suitable electrically insulated lead 11. In other embodiments of the system, the system may also include an electrical charge storage device 8 suitably coupled to the rectifying circuitry 6 for storing the electrical charge flowing through the terminals 10A and 10B of the current rectifying circuitry 6.

The electrical charge stored in the charge storage device 8 (which may to be, for example, a rechargeable battery or electrochemical cell, a capacitor or a super-capacitor, or any other suitable charge storing device) may be supplied as a DC electrical current to an implanted device (for example, to a retinal implant implanted in the eye). In some embodiments of the system, the permanent magnet(s) 2 may be fixed (not moving) within or relative to the first is body part and the inductor(s) 4 may be movable with or by the second body part. For example, the permanent magnet(s) 2 may be non-movably implanted in the skull bones of the eye-socket surrounding the eye and the inductor(s) 4 may be implanted within the eye and may be moved with the eye due to saccadic eye movements and/or any other eye movements, including voluntary eye movements (such eye movements may be in any direction, including but not limited to, up, down and lateral movements and any other movements that are non-mutually exclusive combinations of the above movement directions).

However, it will be appreciated that the word "fixed" refers herein to being fixed with respect to a particular body part. Thus, while a magnet may be fixed and immovable with respect to a skull bone (such as, for example, the maxillary bone) in which it is embedded or implanted, the magnet may still move in three dimensional space, if the entire body to which the skull belongs moves in three dimensional space. In other embodiments of the system, the permanent magnet(s) 2 may be movable with the first body part and the inductor(s) 4 may also be movable by the second body part. For example, the permanent magnet(s) 2 may be attached to or implanted within the eyelid and may be moved together with the eyelid during blinking of the eyelid, and the Inductor(s) 4 may be implanted within the eye and may be moved with the eye due to saccadic eye movements and/or other (voluntary and/or non-voluntary) eye movements as disclosed hereinabove.

A particularly preferred set of embodiments of the present invention relate to an energy harvesting apparatus for harvesting energy from relative motion of an eyeball and an eyelid, primarily during the natural repetitive blinking motion of the eyelid, to drive an electrical device. Referring generically to these embodiments, they typically generally include a coil of conductive wire with an associated support arrangement for supporting the coil in or on an eyeball. The support arrangement may be any support arrangement appropriate for the particular implementation, including but not limited to, a mechanical support or "former" for the coil, a layer of material into which the coil is embedded or onto which the coil is printed or otherwise applied, and a quantity of adhesive for affixing the coil to a surface, all as will be clearer from the examples below and within the capabilities of a person ordinarily skilled in the art.

A permanent magnet is configured for deployment in (by implantation) or on (such as by adhesive) an eyelid, and generates a magnetic field oriented to generate a variation of magnetic flux through the coil on blinking motion of the eyelid.

Rectifying circuitry is electrically connected across the coil and is configured to rectify an electrical output of the coil to generate a DC output for driving the electrical device. Energy from this DC output may be stored in an electrical storage component electrically connected to the rectifying circuitry. The electrical storage component may be part of the energy harvesting apparatus, or may be a component of the electrical device. In some cases, the entire energy harvesting apparatus is implemented as an integrated part of the electrical device. Voltage boosting circuitry may be provided to improve efficiency of charging the electrical storage component.

In some cases, the support arrangement is configured to be applied to an external surface of the eyeball, for example, being integrated with a contact lens that is applied to an external surface of the eyeball. In other cases, the support arrangement is configured to be deployed intraocularly, such as by integration with an intraocular lens. Other examples of intraocular deployment of the coil and/or other components of the apparatus include, but are not limited to: in the cornea (for example, embedded in the same manner conventionally used for corneal inlays or intrastromal corneal ring segments; within the vitreous body of the eye, the anterior chamber, the sulcus or the capsular bag; within the posterior chamber of the eye; within or under the conjunctiva of the eye; and within or under the sclera of the eye.

In a range of different implementations, the coil is advantageously deployed encircling an optic axis of the eyeball, thereby providing a relatively large coil area without disrupting vision.

Figure 2:
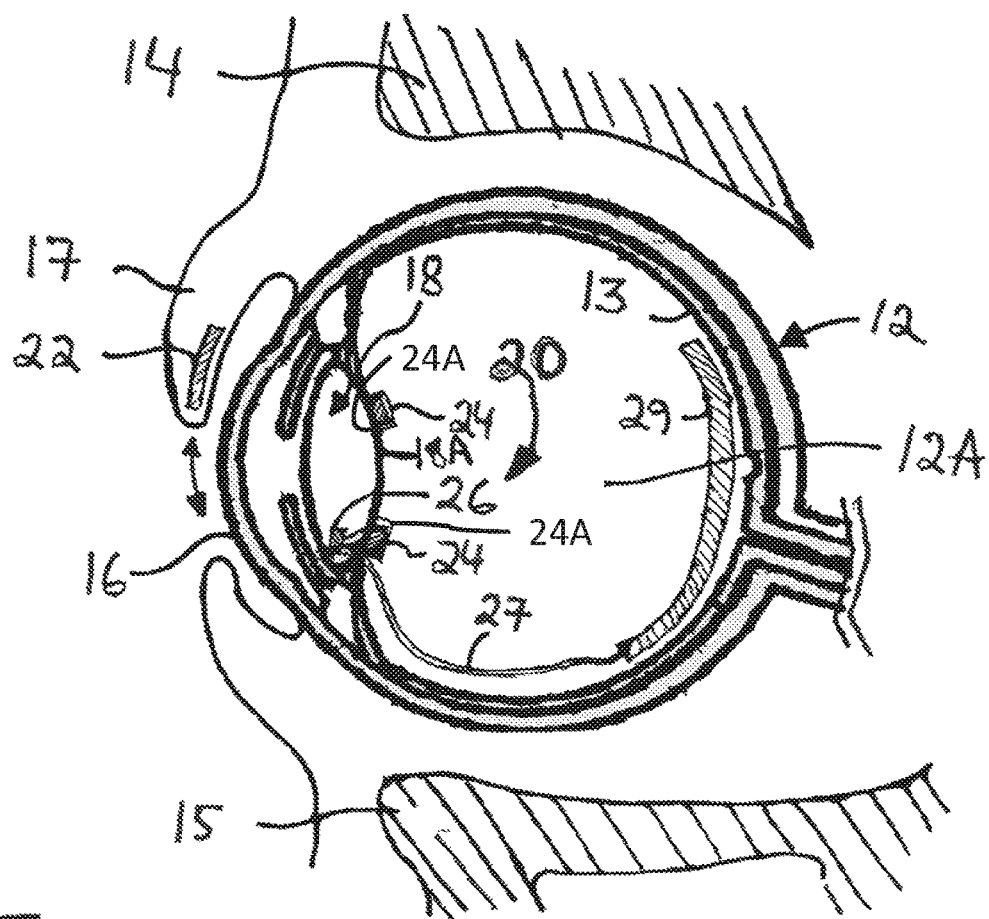
FIG. 2 is a schematic cross sectional diagram illustrating an exemplary embodiment of the system for supplying electrical energy to a retinal implant.

Reference is now made to FIG. 2 which is a schematic cross sectional diagram illustrating an exemplary embodiment of the system for supplying to electrical energy to a retinal implant.

The system 20 includes a permanent magnet 22, shown here as implanted within the upper lid 17 of the eye 12. As an exemplary application, the system 20 as shown here also includes an artificial intraocular lens 18 implanted within the eye 12. The retina 13, the cornea 16, part of the frontal bone 14 and the upper part of the maxillar bone 15 are also illustrated in FIG. 2. The system 20 also includes a coil 24 which functions as an inductor. The coil 24 includes multiple windings, preferably more than 100, of an electrically insulated electrically conducting wire (the wires are not shown in detail in the cross-sectional view of FIG. 2 for the sake of clarity of illustration). The coil 24 may be suitably attached to the rear surface 18A of the implanted intraocular lens 18 as illustrated in FIG. 2. Optionally, a soft magnetic core, typically in the form of a hollow cylinder 24A, may be deployed inside coil 24, optionally as a lining or former for the coil. In some alternative embodiments, the coil 24 may be directly printed on the surface 18A (not shown in FIG. 2).

In some embodiments, the coil 24 may be embedded within the lens 18 (not shown in FIG. 2). The system 20 may also include a miniaturized power conditioning and storage unit 26. The unit 26 includes all the necessary components (not shown in detail in FIG. 2) for current rectifying and for electrical charge storing, as disclosed hereinabove and further detailed below, which may include voltage boosting for effective charging. The unit 26 may be implemented as disclosed in detail hereinabove for the current rectifying circuit 6 and the charge storage device 8 of FIG. 1. The unit 26 may be embedded within the artificial intraocular lens 18, as illustrated in FIG. 2. Optionally, in some embodiments, the unit 26 may also be attached to the surface 18A of the artificial lens 18 (e.g., near the peripheral part of the lens 18) or may alternatively be disposed within another part of the eye 12 (such as, for example within the vitreous body 12A). The coil 24 is suitably electrically connected to rectifying circuitry included in the unit 26 (as shown schematically in FIG. 1 for the inductive element 4 and the current rectifying circuit 6). The system 20 may also include a suitable insulated current output lead 27 that may include suitable electrically insulated electrically conducting wires for supplying direct current from a charge storage device (not shown in detail in FIG. 2) included within the unit 26 (the wires within the lead 27 are not shown in FIG. 2 for the sake of clarity of to illustration).

In the embodiment illustrated in FIG. 2, the system 20 is suitably electrically connected to a retinal implant 29 through the lead 27 for providing electrical power to the retinal implant 29. The retinal implant 29 is not a part of the system 20 and the lead 27 may be suitably electrically connected to any other type of intra-ocular implant for providing electrical power to such an implanted device. In operation of the system 20, when the upper lid 17 opens and closes (blinks), the permanent magnet 22 moves together with the upper lid 17 relative to the coil 24. Additionally and/or alternatively, the coil 24 may move independently of the movements of the upper lid 17 and the permanent magnet 22 due to saccadic eye movements and/or due to any other type of voluntary or involuntary eye movements. As a result of such movements, the position and/or the orientation of the permanent magnet 22 relative to the coil 24 repeatedly change.

The changes in the position and/or orientation of the permanent magnet 22 relative to the coil 24 (which may include changes in the distance between the permanent magnet 22 and the coil 24) result in changes in the magnetic flux passing through the coil 24. As a result of such magnetic flux changes, electrical currents may flow within the coil 24. The current flow may be pulsatile and may flow at different time instances in opposite directions within the coil (i.e. the electrical current flow within the coil 24 may be an alternating pulsatile current).

The unit 26 rectifies the current to provide full wave rectification or half wave rectification of the currents, depending on the specific type or rectifying circuitry used in the unit 26. The rectified current may advantageously then be fed to the charge storage device component included in the unit 26 and may be stored within the charge storage device. The retinal implant 29 may draw electrical power from the charge storage device included in the unit 26 as needed. In some embodiments, the implant (e.g., retinal implant) may include the charge storage device component.

Figure 3:
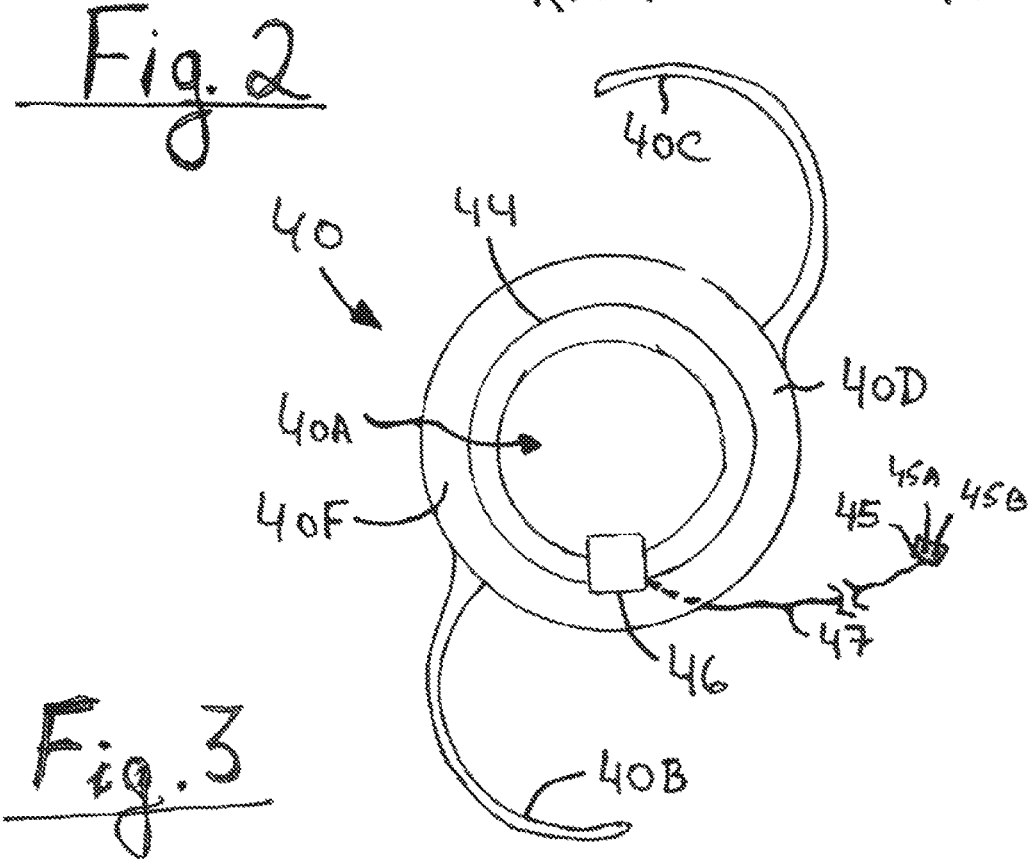
FIG. 3 is a schematic front view of an artificial implantable intra-ocular lens (IOL) including some of the components of the system illustrated in FIG. 1 and suitable for use in the systems of the present application.

Reference is now made to FIG. 3 which is a schematic front view of an artificial implantable intra-ocular lens including some of the components of the system illustrated in FIG. 1 and suitable for use in the systems of the present application. The intraocular lens (IOL) 40 may be made from any suitably transparent biocompatible material suitable for long term intraocular implantation. For example, the IOL 40 may be made from polymethylmethacrylate (PMMA), or from a polysilane based material, or from a hydrophilic polyacrylate based polymer, and/or from any other suitable biocompatible material or mixture of biocompatible polymers or copolymers. The IOL 40 may include an optic part 40A which may be optically transparent and a haptic part or haptic parts for anchoring the IOL 40 in place during implantation. In the exemplary embodiment of the IOL 40 of FIG. 3, the haptic parts of the IOL 40 includes two elongated flexible curved members 40B and 40C that are attached to the periphery 40D of the optic part 40A or alternatively, are implemented as an integral part of the IOL 40.

The IOL 40 may also include a spiral coil 44 that is attached to or printed on the front surface 40F of the IOL 40 (the surface that faces the cornea 16 after implantation of the IOL 40 within the eye 12. Alternatively, in some embodiments the coil 44 may be embedded within the IOL 40. The IOL 40 may also include a power conditioning and storage unit 46 which may be attached to the front surface 40F or may alternatively be embedded within the material of the IOL 40. The power conditioning and storage unit 46 may be suitably electrically connected to the terminals of the coil 44 (the connections are not shown in detail in the front view as they are disposed on the side of the unit 46 facing the coil 44). The power conditioning and storage unit 46 may be similar in construction and operation to the power conditioning and storage unit 26 of FIG. 2, as disclosed in detail hereinabove. An insulated lead 47 is suitably electrically connected to the output terminals of the power conditioning and storage unit 46 (the connection of the wires in the lead 47 are not shown in detail in FIG. 3, as they are also disposed on the side of the unit 46 facing the coil 44, but may be similar to in the connections of the lead 11 of FIG. 1). The lead 47 may terminate in a suitable connecting pad 45 having two contact terminals 45A and 45B.

The contact terminals may be electrically connected to the power receiving terminals (not shown) of any intraocular device (not shown in FIG. 3) implanted within the eye 12 (such as, for example, the retinal implant 29 of FIG. 2) to provide electrical power to the implanted device.

Figure 4:
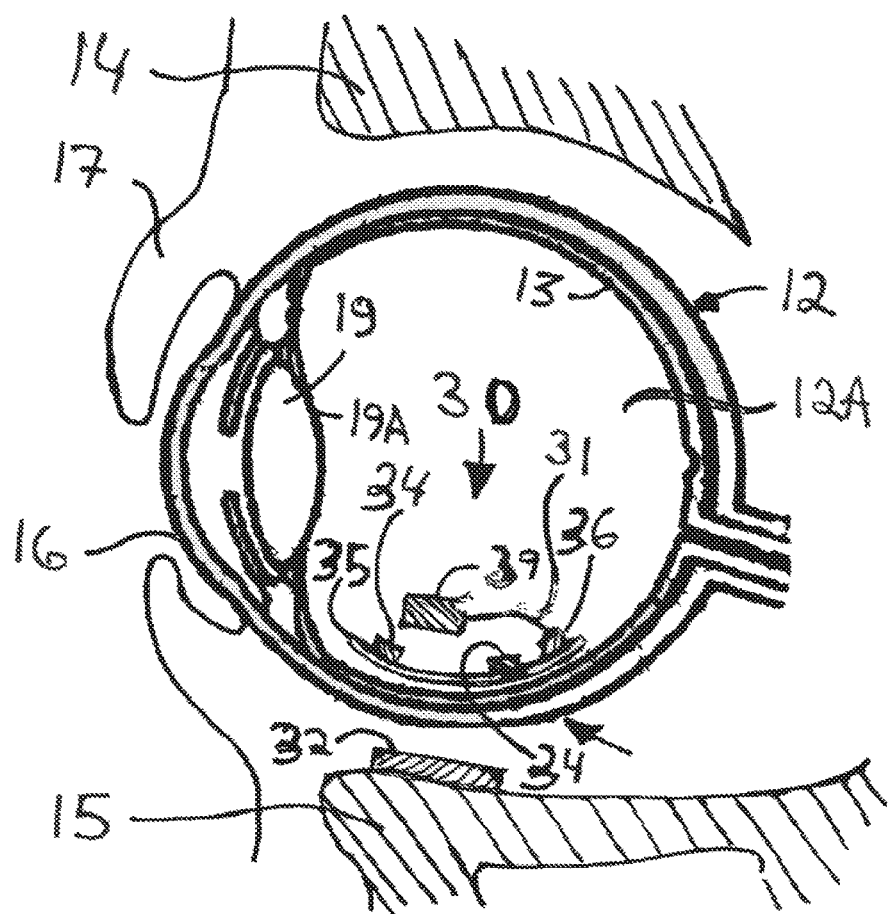
FIG. 4 is a schematic part cross sectional diagram of another embodiment of a system for supplying electrical energy to an implanted intraocular device.

Reference is now made to FIG. 4 which is a schematic part cross sectional diagram of another embodiment of a system for supplying electrical energy to an implanted intraocular device. The Eye 12 has a lens 19 which is positioned between the retina and the cornea. The retina 13 and the vitreous body are also illustrated in FIG. 4. The system 30 may include a permanent magnet 32, fixedly and immovably attached to, e.g., the maxillary bone 15 (or, alternatively immovably implanted within the maxillary bone 15, in some embodiments). The system 30 also includes a coil 34 attached to (or, alternatively, printed upon, or alternatively embedded within) an anchoring member 35. The anchoring member may be made from any suitable implantable biocompatible material, such as, for example, PMMA, a polysilane based material, a hydrophilic polyacrylate based polymer, and/or from any other suitable biocompatible material or mixture of biocompatible polymers or copolymers.

The structure of the coil 34 may be similar to the structure of the coil 24 of FIG. 2 or to the structure of the coil 44 of FIG. 3. The system 30 also includes a power conditioning and storage unit 36 which may be attached to the surface of the anchoring member 35 as illustrated in FIG. 4. The power conditioning and storage unit 36 may be similar in construction and operation to the power conditioning and storage unit 26 of FIG. 2, as disclosed in detail hereinabove. Alternatively, in some embodiments, the power conditioning and storage unit 36 may also be attached to any other suitable part of the eye 12 (such as for example, the retina 13, or any other suitable intraocular structure) and may also be disposed within the vitreous body 12A. The coil 34 is suitably electrically coupled to a current rectifying circuit (not shown in detail in FIG. 4) included within the power conditioning and storage unit 36 by suitable electrically insulated electrically conducting wires (the wires are not shown in detail in FIG. 4, for the sake of clarity of illustration, but may be implemented as illustrated in FIG. 1 with respect to the electrical connection of the inductive element 4 and the rectifying circuit 6).

Alternatively, in some embodiments, the electrical conductors connecting the coil 34 with the current rectifying circuit that is included within the power conditioning and storage unit 36 may be electrical conductors printed on the surface of the anchoring member 35 and covered by a suitable biocompatible insulating material. A lead 31 including suitably insulated electrically conducting wires electrically connects the power output terminals (not shown in detail) of the power storage device (not shown in detail) included within the power 1o conditioning and storage unit 36 with the power input terminals (not shown in detail) of an implanted intraocular device 39, disposed within the vitreous body 12A of the eye 12. For example, the device 39 may be a device for controllably releasing a drug and/or a therapeutic substance and/or therapeutic composition into the vitreous body 12A. The device 29 and any other device that may be powered by the systems of the present application may be a device for controllably releasing a drug. In operation of the system 30, when the eye 12 moves within the eye socket (either due to saccadic eye movements and/or due to other voluntary and/or involuntary eye movements, the coil 34 moves with the eye, while the permanent magnet 32 remains stationary relative to the maxillary bone 15 (being attached to or embedded within the maxillary bone 15). As a result of such movements of the coil 34 relative to the permanent magnet 32, the position and/or the orientation of the coil 34 relative to the permanent magnet 32 may repeatedly change. The changes in the position of the coil 34 relative to the permanent magnet 32 (which may also include changes in the distance between the permanent magnet 32 and the coil 34) may result in changes in the magnetic flux passing through the coil 34. As a result of the magnetic flux changes, electrical currents may flow within the coil 34.

The current flow in the coil 34 may be pulsatile and may flow in opposite directions within the coil 34 depending on whether the coil movement reduces or increases the magnetic flux passing within the coil 34 (i.e. the current flow within the coil 34 may be an alternating pulsatile current). A rectifying circuit (not shown) that may be included in the power conditioning and storage unit 36 rectifies the current flowing in the coil 34 to provide full wave rectification or half wave rectification of the currents, as disclosed hereinabove with respect to the system 20. The rectified current is then fed to a charge storage device component included in the power conditioning and storage unit 36 and is stored within the charge storage device (not shown in detail in FIG. 4, but similar to the charge storage device 8 of FIG. 1).

The implanted device 39 may draw electrical power from the charge storage device included in the power conditioning and storage unit 36 as needed.

Unless otherwise defined, all technical and/or scientific terms used herein have the same meaning as commonly understood by one of ordinary skill to in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are is illustrative only and are not intended to be necessarily limiting. Implementation of the method and/or system of embodiments of the invention can involve performing or completing selected tasks manually, automatically, or a combination thereof.

Moreover, according to actual instrumentation and equipment of embodiments of the method and/or system of the invention, several selected tasks could be implemented by hardware, by software or by firmware or by a combination thereof using an operating system. For example, hardware for performing selected tasks according to embodiments of the invention could be implemented as a chip or a circuit. As software, selected tasks could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions.

Optionally, the data processor includes and/or is operably associated with a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. It is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways. It is expected that during the life of a patent maturing from this application many relevant medical devices and/or systems, circuitry for current rectification and charge storage devices will be developed and the scope of the medical devices and/or systems circuitry for current rectification and charge storage devices of to the present application is intended to include all such new technologies a priori.

As used herein the term "about" refers to ±10%. The word "exemplary" is used herein to mean "serving as an example, instance or illustration." Any particular embodiment of the invention may include a plurality of "optional" features unless such features conflict. The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

EXAMPLES

Various embodiments and aspects of the present invention as delineated hereinabove and as claimed in the claims section below find experimental support in the following examples.

Example 1

Figure 5:
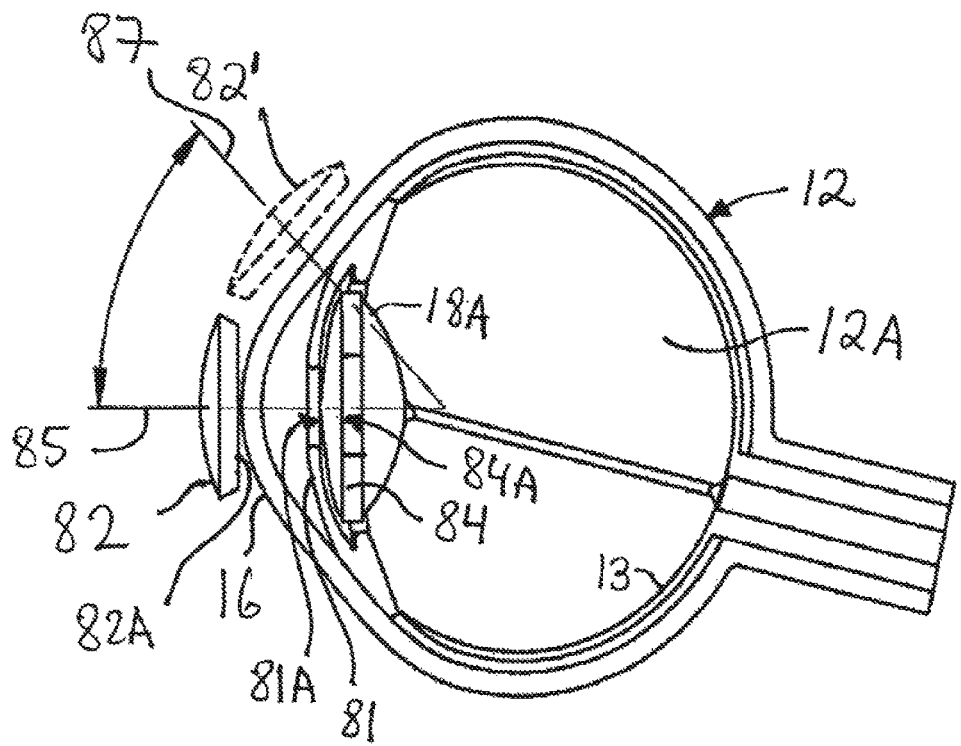
FIG. 5 is a schematic cross-sectional diagram illustrating the effect of upper lid movements on the position of a permanent magnet relative to a coil inductor implanted within the eye, in accordance with some embodiment of the systems of the present application.

Reference is now made to FIG. 5 which is a schematic cross-sectional diagram illustrating the effect of upper lid movements on the position of a permanent magnet relative to a coil inductor implanted within the eye, in accordance with an exemplary embodiment of the systems of the present application.

It is noted that for the sake of clarity of illustration, only the permanent magnet and the inductor of the system are shown in FIG. 5. An inductor in the form of a coil 84 is disposed within the lens sac 18A. The coil 84 has a circular opening 84A therein that has a diameter that is larger than the diameter of a fully dilated pupil 81A of the iris 81. This arrangement allows light rays (not shown) entering the pupil 81A to reach the retina 13 without occluding any light rays by the coil 84. The dimensions of the coil 84 are arranged to fit into the lens sack 18A. A permanent magnet 82 is implanted within or attached to the upper lid (the lid is not shown for the sake of clarity of illustration) of the eye 12. The magnet 82 may have a diameter that is proportional to the diameter of the coil 84 in order to provide increased power output. The thickness of the magnet 82 is such that fits within the eyelid. The magnet 82 may be curved such that the curvature of the surface 82A of the magnet 82 is concave and fits the curvature of the of the eye 12.

In operation, when the upper lid is closed, the position of the magnet 82 is as illustrated by the solid line 82. When the upper lid is opened, the magnet 82 moves into the position illustrated by the dashed line 82'. Blinking significantly changes the distance between the magnet 82 and the coil 84 and the orientation of the magnet 82 relative to the axis 85 passing through the coil 84. The changes caused by the movement of the magnet 82 relative to the coil 84 result in changes in the magnetic flux within the coil 84. In addition to blinking, changes in the position and orientation of the magnet 82 and the coil 84 relative to each other may also be caused by movements of the eye 12.

Figure 6:
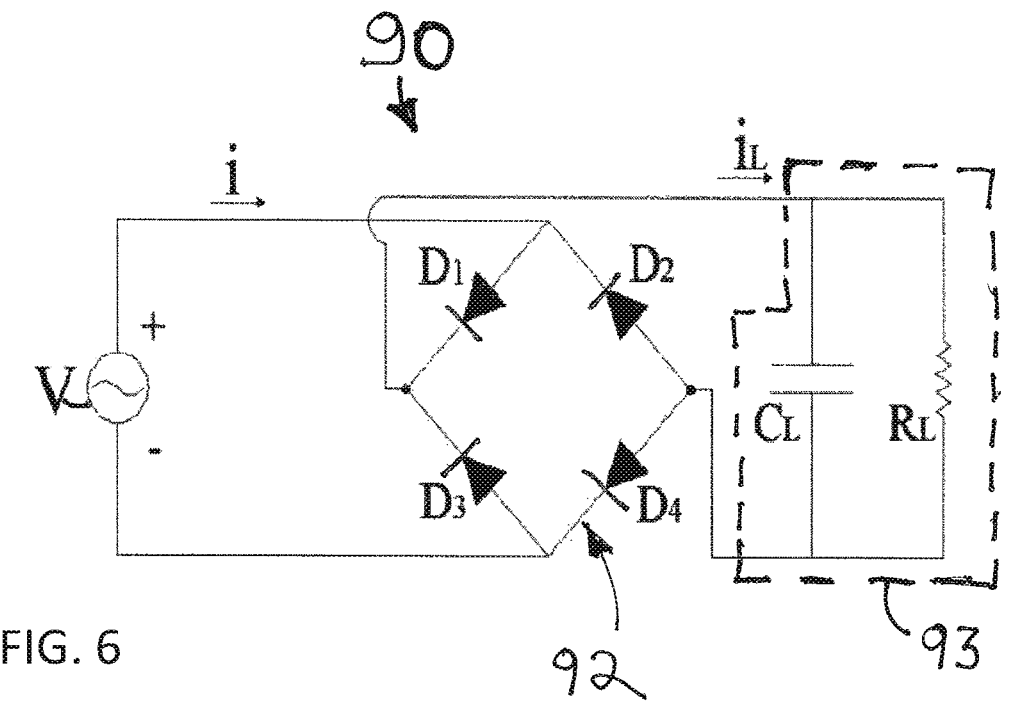
FIG. 6 is a schematic electrical diagram illustrating a system for providing energy to a device electrically coupled to a non-controlled current rectifier circuit and a device coupled to the rectifier and electrically energized by the system.

Such movements may be voluntary eye movements for directing the direction of gazing of the eye and/or involuntary eye movements such as eye saccades. The EMF voltage V(t) which arises from the relative velocity between the magnet 82 and the coil 84 produced by blinking is equal to $$V(t) = \frac{\partial \phi(t)}{\partial t}$$

where ϕ(t) is the magnetic flux flowing through the coil 84 as a function of time. In the case of a permanent magnet and a coil the equation can be formulated as follows $$V(z(t)) = \frac{d\phi(z)}{dz} \frac{dz(t)}{dt}$$

wherein,

V(z(t)) is the electromotive force, dϕ(z) is magnetic flux differential as a function of its position along the coil's path relative to the magnet, and z is the coordinate representing the path of coil relative to the magnet. In FIG. 6 It is the linear path along the arc the magnet under goes, nevertheless z is the arbitrary path that the coil/magnet does relative to each other.

The EMF V(z(t)) is a function of the gradient of the magnetic flux and the relative velocity relative velocity of the magnet with respect to the coil.

The pulsatile alternating current produced by the movements of the magnet 82 and the coil 84 relative to each other may require rectification before being fed to any charge storage device.

Reference is now made to FIG. 6, which is a schematic electrical diagram illustrating a system for providing energy to a device electrically coupled to a non-controlled current rectifier circuit and a device coupled to the rectifier and electrically energized by the system.

The circuit 90 includes an alternating current (AC) source V which may be any of the embodiments of the systems for providing power disclosed in the present application. The AC source V provides the EMF (which may be in the form of pulsatile alternating currents) The AC source V is suitably electrically coupled to a diode H-bridge rectifier 92 including four diodes D1, D2, D3 and D4. The device being energized (the load) is suitably electrically coupled to the diode H-bridge rectifier 92 to receive rectified current therefrom. The device 93 being energized is schematically represented by a load capacitance $C_L$ and a load resistance $R_L$. The AC source V produces an alternating current generated in response to changes in the magnetic flux within the coil(s) of the system resulting from changes in the position and/or orientation of the permanent magnet(s) and/or the coil(s) of the system relative to each other as disclosed in detail hereinabove. The AC current I is rectified by the diode H-bridge rectifier 92 and the rectified current $I_L$ flows into the device 93 to be energized.

It is noted that, in some embodiments, the EMF may be too low for the rectifier to work efficiently and/or to achieve effective charging of the electrical storage component. In such cases, a boost might be needed to up-convert the voltage output and lower the currents. A number of technologies may be employed to achieve a boost in the voltage to enhance charging, and each may be used alone or in combination with the others.

Firstly, it is noted that the voltage output from the coil due to the eye movement is a transient one, and is therefore a sum of multiple harmonics. The output voltage can therefore be increased by employing a transformer arrangement prior to rectification.

Figure 7:
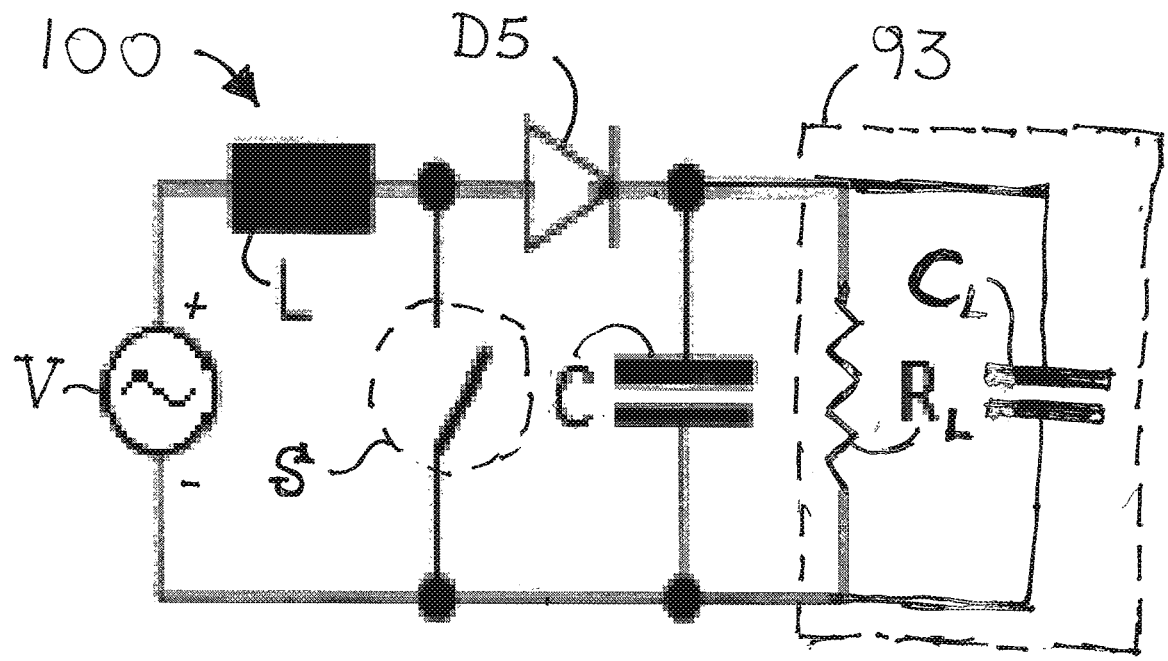
FIG. 7 is a schematic circuit diagram illustrating a switch based DC-DC boost converter, electrically connected between an AC source V, and the device to be energized.

Additionally, or alternatively, an arrangement for DC-DC voltage boosting may advantageously be employed. Reference is now made to FIG. 7, which is a schematic circuit diagram illustrating a switch-based DC-DC boost converter, electrically connected between the AC source V, and the device 93 to be energized. The DC-DC boost converter may include an inductor L, a capacitor, a switch S and a diode D5. The booster circuit operates in two stages. In the first stage, the switch S is closed and the inductor L charges up as the entire current flows through the inductor L only. In the second stage, the switch S is opened. The charge in the inductor L charges up the storage capacitor C. With appropriate switching logic (not shown in detail in FIG. 7), the charge in the capacitor C can be maintained near to a constant value. The capacitor $C_L$ and the resistor $R_L$ represent the load capacitance and the load resistance, respectively of the device 93.

The switching of the switch S between the closed state and the opened state may be controlled by a suitable microcontroller or by any other suitable controlling device. Implementations of such DC-DC boost converter circuits may be as disclosed in the article by V. e. a. Balasubramanyam, entitled "Modeling and Simulation of an Energy Harvesting System," *IX Symposium Industrial Electronics INDEL* 2012.

Additional techniques may be used to enhance the output voltage based on principles of frequency, phase and amplitude shaping, as known in the relevant arts.

Permanent Magnet Design

In implementations of the present invention activated primarily by blinking motion of the eyelid, the permanent magnet is preferably formed as a flat or curved slab contiguous (without gaps) in two major dimensions, and having a maximum local thickness small enough to render the size suitable for implantation within the eyelid, or for attachment to an outer surface of the eyelid, as appropriate to the implementation. The (local) thickness of the magnet is preferably no more than 1.5 millimeters, and the major dimensions (or diameter) are preferably similar to, or slightly smaller than, the average diameter of the coil. Typically, each of the two major dimensions (e.g., width and height, or diameter of a circular disk) is at least five times greater than the maximum local thickness.

In one set of implementations, the direction of magnetization of at least part of the permanent magnet, and in some cases, the entirety of the magnet, is substantially perpendicular to both of the two major dimensions. In certain cases, the permanent magnet is formed as a slab having a concave major surface for accommodating a curvature of the eyeball, and a convex major surface. For implementations in which the magnet is attached to the eyelid, an adhesive pad is preferably associated with one of the major surfaces of the permanent magnet.

Three different configurations of permanent magnets have been simulated as follows: a flat disc shaped permanent magnet, a concave (curved) permanent magnet without a ferromagnetic shield, and a concave (curved) permanent magnet with a ferromagnetic shield, and a number of additional magnet configurations are also proposed.

Figure 8:
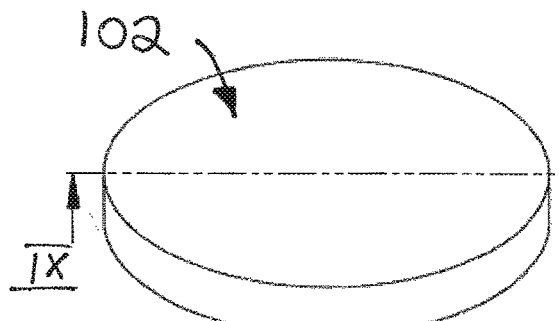
FIG. 8 is a schematic isometric view illustrating a flat disc-like permanent magnet, in accordance with some embodiments of the magnets of the present application.
Figure 9:
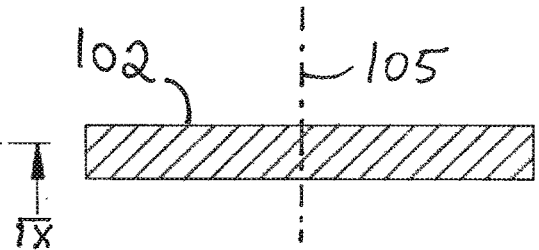
FIG. 9 is a schematic cross-sectional view of the permanent magnet of FIG. 8 taken along the lines IX-IX.
Figure 10:
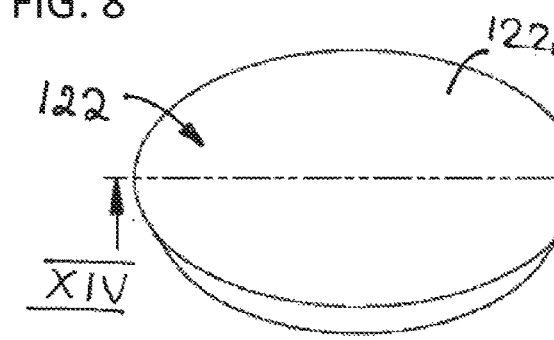
FIG. 10 is a schematic isometric view illustrating a curved concave permanent magnet, in accordance with some embodiments of the magnets of the present application.
Figure 11:
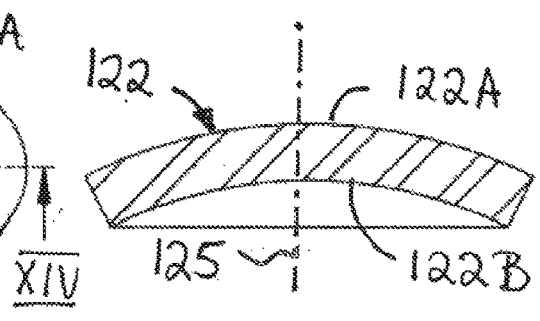
FIG. 11 is a schematic cross-sectional view of the permanent magnet of FIG. 10 taken along the lines XIV-XIV.
Figure 12:
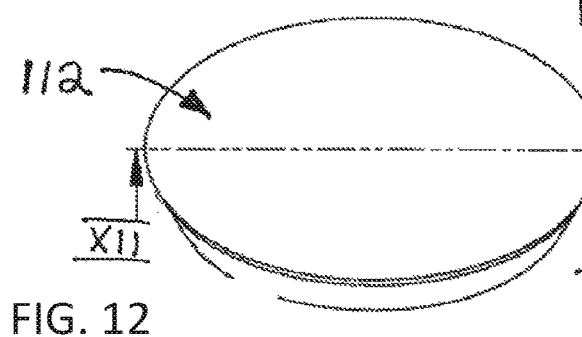
FIG. 12 is a schematic isometric view illustrating a curved concave permanent magnet having a ferromagnetic shield attached to a concave surface of the permanent magnet, in accordance with some embodiments of the magnets of the present application.
Figure 13:
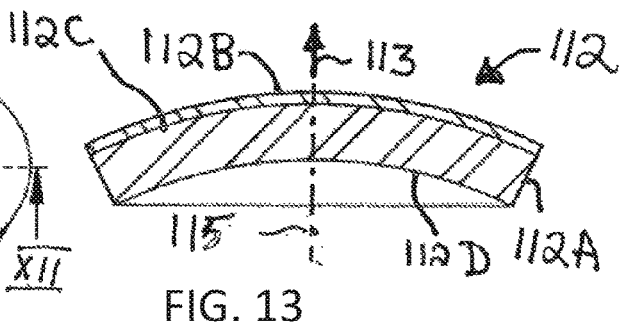
FIG. 13 is a schematic cross-sectional view of the permanent magnet of FIG. 12 taken along the lines XII-XII.
Figure 14:
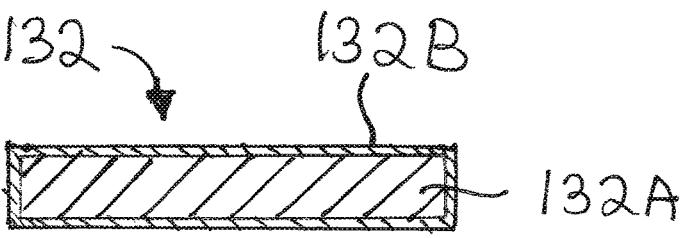
FIG. 14 is a schematic cross-sectional view illustrating a permanent magnet coated with or embedded in a layer of biocompatible implantable material.
Figure 15:
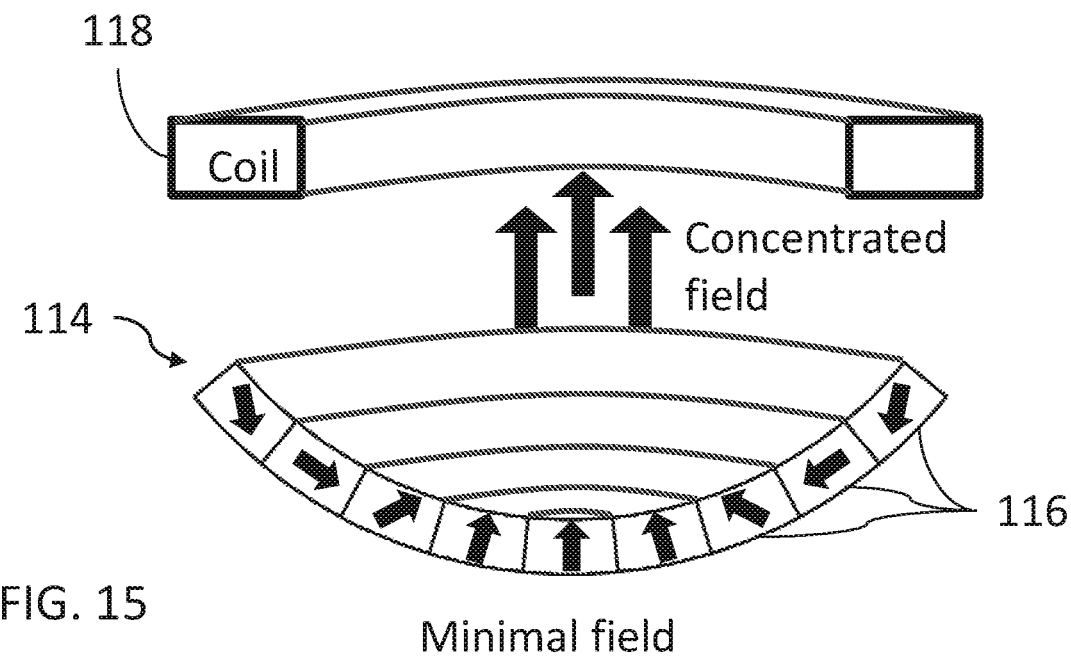
FIG. 15 is a schematic illustration of a variant implementation of the permanent magnet.
Figure 16:
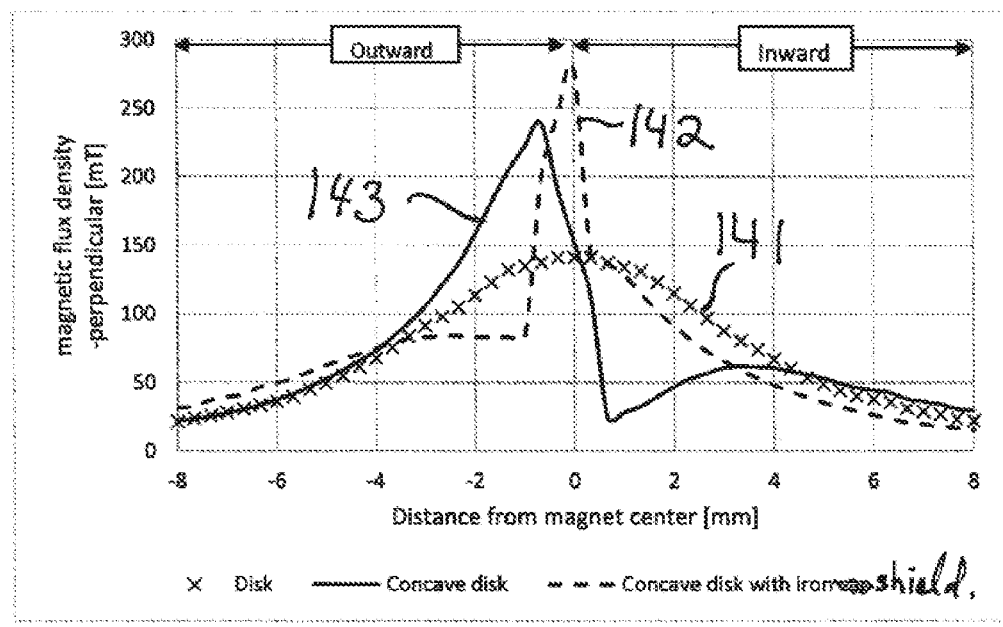
FIG. 16 is a schematic graph illustrating the simulated dependence of the magnetic flux density on the distance from the center of the magnet for the three different types of magnets illustrated in FIGS. 9, 11 and 13.

Reference is now made to FIGS. 8-15. FIG. 8 is a schematic view illustrating a flat disc-like permanent magnet, in accordance with some embodiments of the magnets of the present application. FIG. 9 is a schematic cross-sectional view of the permanent magnet of FIG. 8 taken along the lines X-X. FIG. 10 is a schematic isometric view illustrating a curved concave permanent is magnet, in accordance with some embodiments of the magnets of the present application. FIG. 11 is a schematic cross-sectional view of the permanent magnet of FIG. 10 taken along the lines XIV-XIV. FIG. 12 is a schematic isometric view illustrating a curved concave permanent magnet having a ferromagnetic shield attached to a concave surface of the permanent magnet, in accordance with some embodiments of the magnets of the present application. FIG. 13 is a schematic cross-sectional view of the permanent magnet of FIG. 12 taken along the lines XII-XII. FIG. 14 is a schematic cross-sectional view illustrating a permanent magnet coated with or embedded in a layer of biocompatible implantable material. FIG. 15 is a schematic cut-away isometric view illustrating a further optional implementation of the permanent magnet in which the magnet is implemented as a compound magnet with a plurality of different regions having differing directions of magnetization. FIG. 16 is a schematic graph illustrating the simulated dependence of the magnetic flux density on the distance from the center of the magnet for the three different types of magnets illustrated in FIGS. 8,10 and 12.

Turning to FIGS. 8-9, the permanent magnet 102 is shaped like a flat disc. A symmetry axis 105 passes through the center of the magnet 102. The direction of magnetization is preferably parallel to the symmetry axis 105.

Turning to FIGS. 10-11, the permanent magnet 122 is a curved magnet having a convex surface 122A and a concave surface 122B. When implanted in an eyelid, the concave surface 122B is directed towards the eye and the curvature of the concave surface may be shaped to accommodate the convex curvature of the eye's surface (as illustrated in FIGS. 2 and 6). A symmetry axis 125 passes through the center of the magnet 122. Here too, a preferred direction of magnetization is typically parallel to symmetry axis 125. Alternatively, a radial direction of magnetization, i.e., perpendicular to the surface across the concave surface, may be advantageous. (Additional more complex patterns of magnetization will be discussed below with reference to FIG. 15.)

Turning to FIGS. 12-13, the permanent magnet 112 is a curved magnet which includes a curved permanent magnet 11A and a curved ferromagnetic shield 112B. The curved ferromagnetic shield 112B is attached to the convex surface 112C of the permanent magnet 112A. The attaching of the ferromagnetic shield 112B to the permanent magnet 112A may be performed by gluing with a suitable adhesive or by any other suitable attaching method. A symmetry axis 115 passes through the center of the magnet 112.

In permanent magnets implantable in the upper lid of the eye, the curvature of the concave surface 112D of the permanent magnet 112A may be shaped to accommodate the convex curvature of the eye's surface (as illustrated in FIGS. 2 and 6). The ferromagnetic shield 112B is used for reducing the intensity of external magnetic field (directed in the direction represented by the arrow 113). This feature may be advantageous as it may prevent metallic objects from becoming attracted to the external surface of the eyelid when the permanent magnet 112 is implanted within a lid.

A major contribution of the ferromagnetic shielding is reducing magnetic flux leakage and concentrating the magnetic flux to increase efficiency and create denser magnet flux lines thus enlarging the flux's gradient.

FIG. 15 illustrates a variant implementation of the permanent magnet as a compound permanent magnet 114 having a plurality of different regions of magnetization 116 with differing directions of magnetization. The compound magnet employs the principles of a Halbach array to generate a shaped magnetic field with enhanced flux intensity along an inwards-facing direction (i.e., inwards from the concave surface) from said compound permanent magnet, thereby enhancing flux variation during motion of the magnet relative to a coil 118. The Halbach array approach inherently reduces magnetic field on the opposite (convex) side, thereby providing advantages similar to those described above with respect to the shielding of FIGS. 12-13. The relative sizes of the regions 116 and their directions of magnetization can be chosen, analytically and/or by straight forward experimental techniques, to optimize the flux pattern and flux intensity for any given placement of the magnet relative to the coil.

Although illustrated in a concave/convex form without shielding, similar to FIG. 10, it should be noted that the compound permanent magnet implementation of FIG. 15 may be used with a flat or curved magnet configuration, with or without shielding as illustrated in FIG. 12, and with or without non-magnetic biocompatible coating as in FIG. 14.

It is noted that the permanent magnet(s) used in the systems of the present application may be made from any suitable type of permanently magnetized material(s) and may optionally also include ferromagnetic materials (as illustrated in the example of FIG. 11). In some embodiments magnetic metamaterials may be used. It is noted that the magnets of the systems of the present application may be arbitrarily shaped in accordance with some non-limiting examples of the permanent magnets, the permanent magnets may be made of or may include permanently magnetized materials such as, iron neodymium boron (FeNdB), samarium-cobalt (SmCo), ceramic permanently magnetized material(s) or any other type of suitable permanently magnetized material(s). The permanent magnets may also (optionally include, one or more parts made of a ferromagnetic material, such as, for example iron (Fe), nickel (Ni), Cobalt (Co), Permalloy (Nickel-Iron alloys) or any other suitable ferromagnetic material). Such ferromagnetic materials may be used for shaping or modifying the magnetic field of the permanent Magnet(s) as disclosed in detail in FIGS. 12-13, hereinabove.

It is further noted that the number, shapes, dimensions and magnetic properties of the permanent magnet(s) of the systems of the present application may vary, depending, inter alia, on the magnetic and/or ferromagnetic material(s) from which the magnet(s) is/are made, the required magnetic flux parameters, the distance and/or position and/or orientation of the permanent magnet(s) relative to the coil(s) or inductor(s) of the system, and other mechanical, magnetic and electrical considerations. For example, in some embodiments of the system, more than one permanent magnet may be used, in conjunction with one or more inductors. For example, the system 30 of FIG. 4 may be modified by attaching or implanting a second permanent magnet (not shown in FIG. 4) in the frontal bone 14. In some embodiments, the system may include several permanent magnets and a single inductor. In yet some other embodiments, the system may include several permanent magnets and several inductors.

Turning to FIG. 14, the permanent magnet 132 includes a flat disc-like permanent magnet 132A and a layer of protecting material 132B that surrounds the entire surface of the permanent magnet 132A. The permanent magnet 132 may also be embedded in the protective material 132B. In permanent magnets designed to be externally attached to a body part (such as, for example a permanent magnet designed to be attached to an arm, the protecting material may be any suitable type of material for protecting the permanent magnet 132A. Such protective materials may include, for example any suitable type of polymer or polymer based material, an engineering plastic, a thermoplastic polymer, rubber, polybutadiene, a polysilane but any other suitable material may be used. The layer of protecting material 132B may protect the permanent magnet 132A from abrasion or scratches, mechanical shocks, etc.

In permanent magnets designed to be implanted in a part of the body (such as, for example, a lid, a maxillary bone, a frontal bone, a torso, an arm, a leg, or any other body part), the layer of protecting material 132B may be made of or may include a biocompatible material, such as, for example, a biocompatible polymer such as, for example, Parylene-c®, Polyethylene (PE), Polypropylene (PP), polydimethyl siloxane (PDMS), a biocompatible ceramic material, a biocompatible metal or alloy such as, for example, titanium, a titanium alloy, or any other suitable biocompatible material.

It is noted that any type of permanent magnet usable in the systems of the present application may also include a layer of protective material and/or a layer of biocompatible material, as disclosed hereinabove.

It is further noted that the shape and dimensions of the permanent magnets of the present application are not intended to be limited by the shapes and dimensions and magnetic properties of the specific exemplary permanent magnets disclosed in the present application, rather, the dimensions, magnetic properties and shape of the permanent magnets may be varied and may be adapted to the specific application. For example, the permanent magnets may have a circular shape, a disc-like, shape, an elliptical shape, a polygonal shape, a rectangular shape, a square shape, a flat shape, a curved shape, an irregular shape or any other suitable shape.

Turning now to FIG. 16, the graph includes three simulated curves 141, 142 and 143. The vertical axis of the graph represents the magnetic flux density in mT and the horizontal axis of the graph represents the distance (in millimeters) from the center of the permanent magnet.

The curve 141 (denoted by the symbols X) represents the simulation results for the flat disc like permanent magnet 102 of FIGS. 8-9. For the curve 141, the horizontal axis represents the distance from the center of the magnet 102 along the axis 105 (of FIG. 9).

The curve 142 (denoted by the dashed line) represents the simulation results for the circular curved magnetically shielded permanent magnet 112 of FIGS. 12-13. For the curve 142, the horizontal axis of the graph represents the distance from the center of the magnet 112 along the axis 115 (of FIG. 11).

The curve 143 (denoted by the solid line) represents the simulation results for the non-shielded circular curved permanent magnet 122 of FIGS. 10-11. For the curve 143, the horizontal axis of the graph represents the distance from the center of the magnet 122 along the axis 125 (of FIG. 11).

In the simulation results of FIG. 16, the permanent magnets 102,112 and 122 provide similar flux densities further away from the center of the permanent magnet. For the curved magnets 112 and 122, the concavity of the magnet produces a maximum magnetic flux in the outward direction and close to the center of the magnets 112 and 122 and a steeper rate of decrease (steeper negative slope of the curves 142 and 143, respectively) in the magnetic flux density in the inward direction. It may be seen that the presence of the ferromagnetic shield 112B included in the permanent magnet 112 reduces the magnetic flux density close to the eye lid (in the outward direction), effectively lowering the chance that a ferromagnetic object will attach to the eye lid.

The sum of the magnetic flux density flowing through the coil (assuming the same coil is placed +6 mm from the center of the magnet along the symmetry axis (axis 105 for the magnet 102, axis 115 for the magnet 112 and axis 125 for the magnet 122) was calculated for each of the magnets. and is given in TABLE 1 below.

TABLE 1

| | Flat Magnet 102 | Concave magnet 122 | Concave magnet 112 with shield |
|---|---|---|---|
| Magnetic Flux [µWb] | 1.90 | 2.60 | 2.74 |

It may be seen in TABLE 1 that while the summed magnetic flux for the concave magnets 112, and 122 is quite similar (the difference is less than 6% between the curved magnets 112 and 122), the curved magnets 112 and 122 provide an increase of flux density about 37%-44%, respectively as compared to the flux density of the flat magnet 102. The magnetically shielded curved magnet 112 has the additional advantage of having a lower magnetic flux density in the outward direction due to the ferromagnetic shield 112B.

Figure 17:
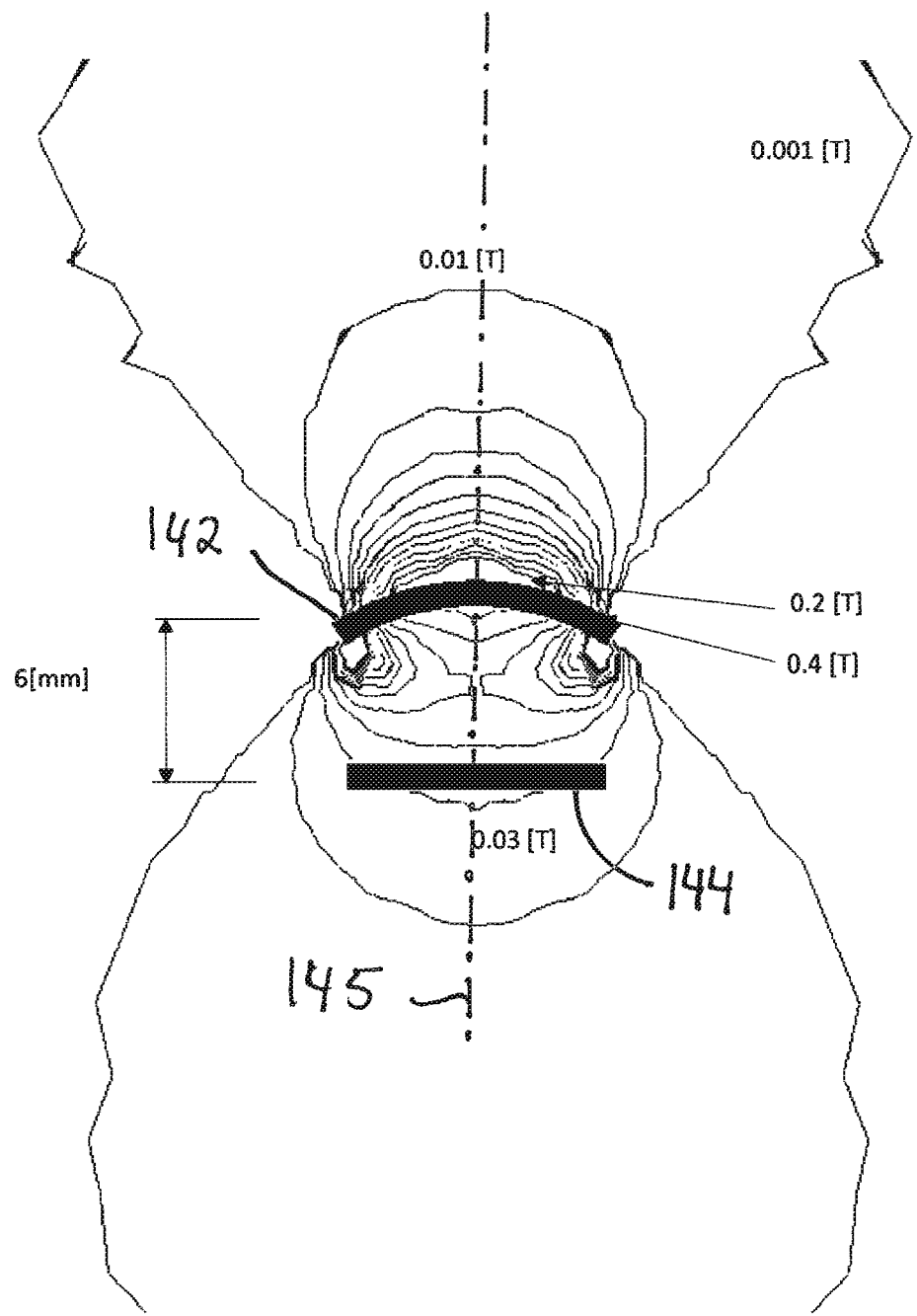
FIG. 17 is a schematic diagram illustrating the simulated magnetic field intensity of a shielded magnet, in accordance with an embodiment of the permanent magnets of the present application.

Reference is now made to FIG. 17, which is a schematic diagram illustrating the simulated magnetic field intensity of a shielded magnet, in accordance with an embodiment of the permanent magnets of the present application. The magnet diameter is 10 mm, magnet thickness is 1 mm, the curvature radius of 9 mm. The material is N52 Neodymium Magnet. The shield has a thickness of 0.1 mm, and material of the shield was selected to be a soft ferromagnetic-alloy.

The position of the permanent magnet 142 and the coil 144 of the simulation are illustrated in FIG. 17 and the contour lines on each side of the symmetry axis 145 represent the intersection of surfaces of equal magnetic flux density with the plane of the page. The numbers in the square brackets represent the magnetic flux density (in Tesla) of some of the contour lines.

Power Output of the System

For a coil type inductor[, the power output $P_{tot}$ of the system for a load with complex impedance $Z_{tot}$ is equal to $$P_{tot} = \frac{V^2}{Z_{tot}} = N^2 \frac{1}{Z_{load} + Z_{coil}} \left(\frac{d\phi(z)}{dz}\right)^2 \left(\frac{dz(t)}{dt}\right)^2$$

wherein

N is the number of coil windings.

V is voltage $Z_{load}$ is the load impedance $Z_{coil}$ is the coil impedance $\phi(z)$ is the total magnetic flux flowing through the coils and, z is the coordinate defining the relative movement between the magnet and the coil.

On the average, the eyelid blinks a distance of approximately 10 mm in 0.3 sec. The value of the relative velocity $V_{rel}$ is approximately calculated to be $$v_{rel} = \frac{2 \times 10}{0.3} = 67 \frac{mm}{sec}$$

Figure 18:
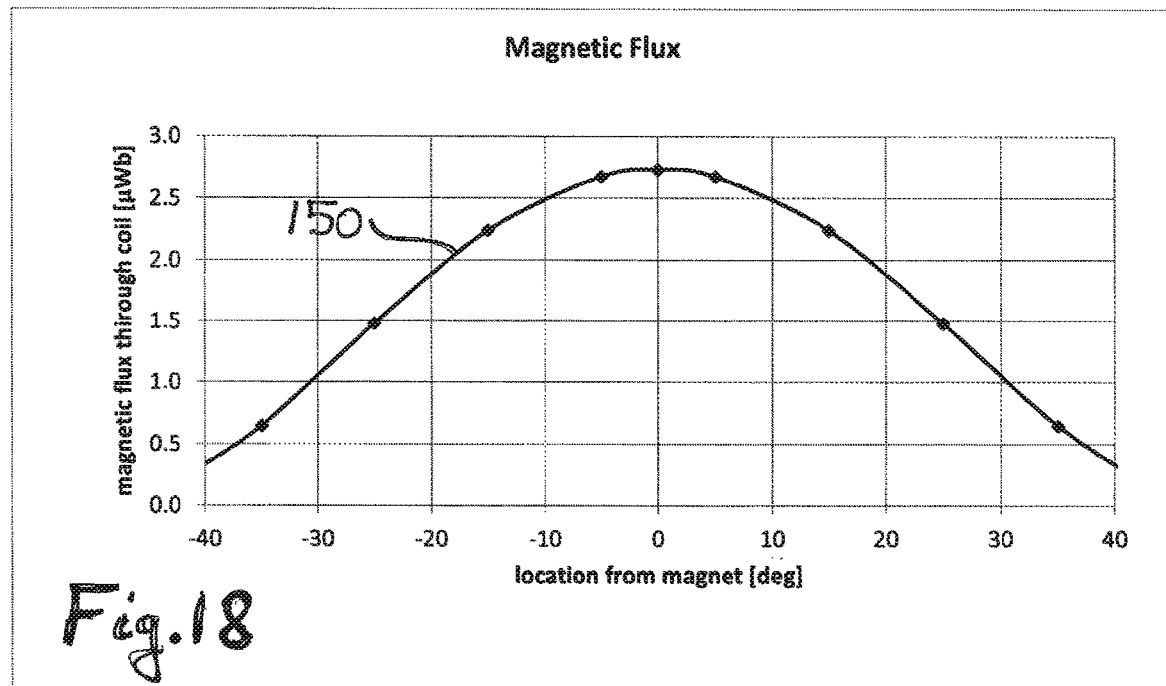
FIG. 18 is a graph illustrating the simulated variation in the magnetic flux through an exemplary coil movable relative to a permanent magnet as the angle between the coil and the magnet changes.
Figure 19:
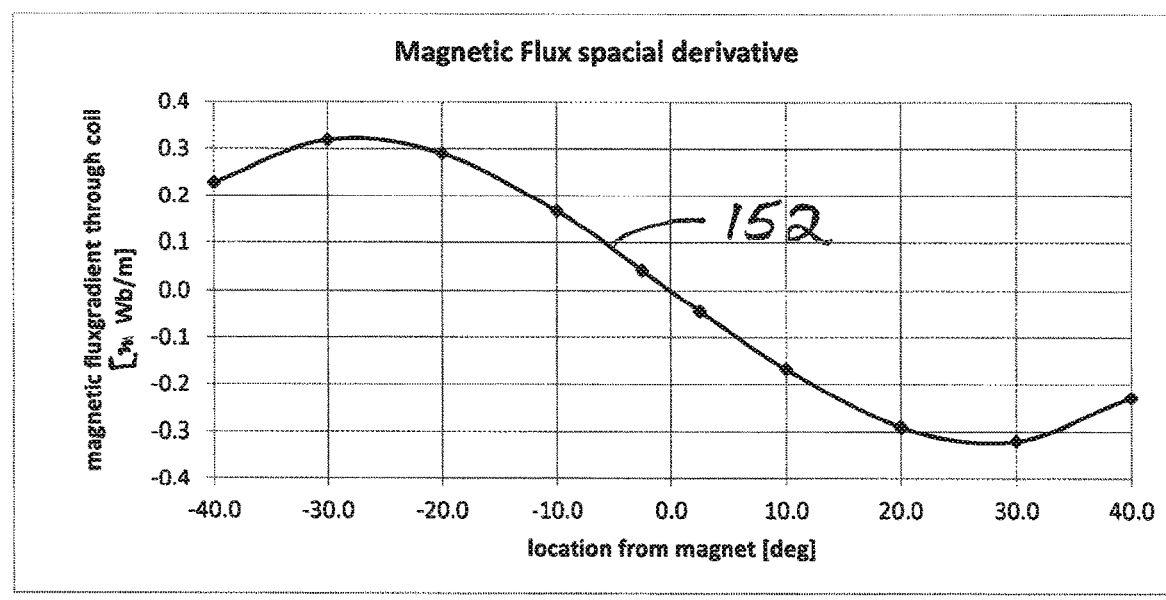
FIG. 19 is a graph illustrating the simulated variation of the flux gradient through the exemplary coil as the angle between the coil and the magnet changes.

Reference is now made to FIGS. 18-19. FIG. 18 is a graph illustrating the to simulated variation in the magnetic flux through an exemplary coil movable relative to a permanent magnet as the angle between the coil and the magnet changes. The vertical axis of the graph in FIG. 18 represents the magnetic flux through the coil in µWb and the horizontal axis of the graph represents the angle between a symmetry axis the permanent magnet (axis 87 of FIG. 5) and a symmetry axis of the coil (axis 85 of FIG. 5). The curve 150 of FIG. 18 represents magnetic flux through the coil as a function of the angle between a symmetry axis the permanent magnet (axis 87 of FIG. 5) and a symmetry axis of the coil (axis 85 of FIG. 5).

FIG. 19 is a graph illustrating the simulated variation of the flux gradient through the exemplary coil as the angle between the coil and the magnet changes. The vertical axis of the graph of FIG. 19 represents the magnetic flux gradient through the coil in mWb/m (milliWeber per meter) and the horizontal axis of the graph represents the angle between a symmetry axis the permanent magnet (axis 87 of FIG. 5) and a symmetry axis of the coil (axis 85 of FIG. 5). The curve 152 of FIG. 19 represents the magnetic flux gradient through the coil as a function as a function of the angle (in degrees) between a symmetry axis the permanent magnet (axis 87 of FIG. 5) and a symmetry axis of the coil (axis 85 of FIG. 5).

The gradient of the magnetic flux was evaluated by the FEM simulation program Ansys, commercially available from ANSYS, Inc., USA.

In FIG. 18, the simulation parameters were as follows:

The total impedance is the sum of the load impedance and the coil's impedance. For optimal power output the impedances are matched.

TABLE 2 and TABLE 3 below provides the parameters used in the simulation and calculations.

TABLE 2

| Parameter | Value | Unit |
| --- | --- | --- |
| Coil's outer diameter | 11.3 | mm |
| Coil's Inner diameter | 5 | mm |
| Coil average diameter | 8.15 | mm |
| coil Height | 1 | mm |
| Coil Turns H | 13 | |
| Coil Turns D | 37 | |
| Coil Turns number N | 481 | |
| Coil length | 12.3 | m |
| Coil Resistance | 42.4 | Ω |
| magnet velocity | 0.07 | m/sec |
| AWG # | 40 | |
| wire D - WO-isolation | 0.080 | mm |
| wire D - W-isolation | 0.086 | mm |
| wire area - WO-isolation | 0.005 | mm$^2$ |
| wire area - W-isolation | 0.01 | mm$^2$ |
| copper conductivity | 5.8 × 10$^7$ | S/m |
| copper density | 8890 | kg/m$^3$ |
| single blink duration | 0.4 | second |
| Average number of blinks per minute | 20 | |
| number of blinks per second | 0.33 | |
| Total blinking time | 0.133 | second |

TABLE 3

| | | Instantaneous Power[µW] | | |
| --- | --- | --- | --- | --- |
| voltage [mV] | current [mA] | Instantaneous Power[µW] | Power total[µW] | Power losses[µW] |
| −7.3E+00 | −1.7E−01 | 0.32 | 0.64 | 0.32 |
| −1.0E+01 | −2.4E−01 | 0.62 | 1.23 | 0.62 |
| −9.3E+00 | −2.2E−01 | 0.51 | 1.02 | 0.51 |
| −5.4E+00 | −1.3E−01 | 0.17 | 0.34 | 0.17 |
| −1.4E+00 | −3.3E−02 | 0.01 | 0.02 | 0.01 |
| 1.4E+00 | 3.3E−02 | 0.01 | 0.02 | 0.01 |
| 5.4E+00 | 1.3E−01 | 0.17 | 0.34 | 0.17 |
| 9.3E+00 | 2.2E−01 | 0.51 | 1.02 | 0.51 |
| 1.0E+01 | 2.4E−01 | 0.62 | 1.23 | 0.62 |
| 7.3E+00 | 1.7E−01 | 0.32 | 0.64 | 0.32 |
| Average Power[µW] (instantaneous) | | 0.33 | 0.65 | 0.33 |
| Average Power[µW] (average) | | 0.04 | 0.09 | 0.04 |
| daily energy (18 hours) [mJ] | | 2.81 | | |

The average power was calculated based on the average period of blinking. The average human blinks about 20 times per minute. The average power output is about 0.04 µW. Such power output is sufficient to operate many types of medical devices and sensors implantable in the eye. As blinking is continuous during waking hours, any excess power may be accumulated and stored in a suitable charge storage device (Such as, for example, the charge storage device 8 of FIG. 1, or any other charge storage device included in the systems disclosed hereinabove or in the medical device being energized). Such stored excess charge may be used when the need arises, such as, for example, when data is being wirelessly transmitted from any transmitter or transceiver included in the device being energized by the systems of the present application.

The systems disclosed herein for providing electrical energy to devices attached to or implanted in an eye may be used to energize various different is types of ocular devices. Exemplary devices which may be energized by such systems may include devices with a sensor such as a pressure sensor for measuring the intraocular pressure, or device that determine glucose levels, level of proteins such as VEGF or oxygen levels. Devices device that may deliver electrical power to the retina such as retinal prosthesis, devices that use electrical or mechanical power to release a drug in a controlled manner, devices that use moving part(s) such as propellers and/or fins to propel or move intraocular fluid, devices that use electrical signal to stimulate the lachrymal gland, devices that uses electrical signal to stimulate the ocular muscles or the palpebral muscles and devices that perform or assist accommodation in an implantable intraocular lens.

The systems disclosed in the present application may also provide electrical power for charging any type of charge storage device (such as a battery, a rechargeable electrochemical cell or a super-capacitor that may (optionally) be included in the system itself or may be included in the medical device. For example such a charge storage device may be included in an intraocular lens or in a "smart" contact lens. The intraocular lens or a contact lens may use this energy for many uses for example for operating a display device included in the IOL or contact lens for displaying images or information to the user, a device for performing accommodation in an IOL, or for changing the optical characteristics of a contact lens.

The systems for providing electrical energy disclosed in the present application may also be used to energize devices that operate to close the eyelid for people with paralysis such as Bell's palsy. Such systems may use the healthy moving eyelid for generating the electrical power for closing/opening of the paralyzed eyelid of the other eye.

Although the apparatus of the present invention is disclosed primarily in the context of harvesting energy from blinking, certain aspects of the implementation may be applied to advantage in other contexts. The systems for providing electrical energy disclosed in the present application may also be adapted for use in various different body parts or artificial prosthetic devices in a body. For example, the inductor(s) of the systems may be installed or attached or implanted in various joints and may utilize the relative movement between any two parts of the joint which are movable relative to each other. For example, in some embodiments, the systems may be installed in a smart artificial joints, such that.

The inductor(s) and permanent magnet(s) of the systems for providing electrical energy of the present application may also be attached to or implanted in various different body parts of the body, using the relative movement of such body part pairs relative to each other. Such body part pairs may include the following pairs of body parts: teeth and cheek, upper teeth and lower teeth, tongue and cheek, tongue to teeth, upper lip and lower lip, a first finger and an adjacent second finger adjacent to the first finger, an arm and part of the body trunk or torso, an arm and a pelvis a first leg and a second leg, a diaphragm an and adjacent organ (such as an aorta).

Devices that may be energized by the energizing systems disclosed in the present application may include smart eye implants, cochlear implants, various nerve stimulation devices including but not limited to, brain stimulating devices, peripheral nerve stimulating devices, vagus nerve stimulating devices, sympathetic nervous system stimulating devices, intestinal electrical stimulation devices and any other type of nervous and/or muscle tissue stimulating devices.

Figure 20:
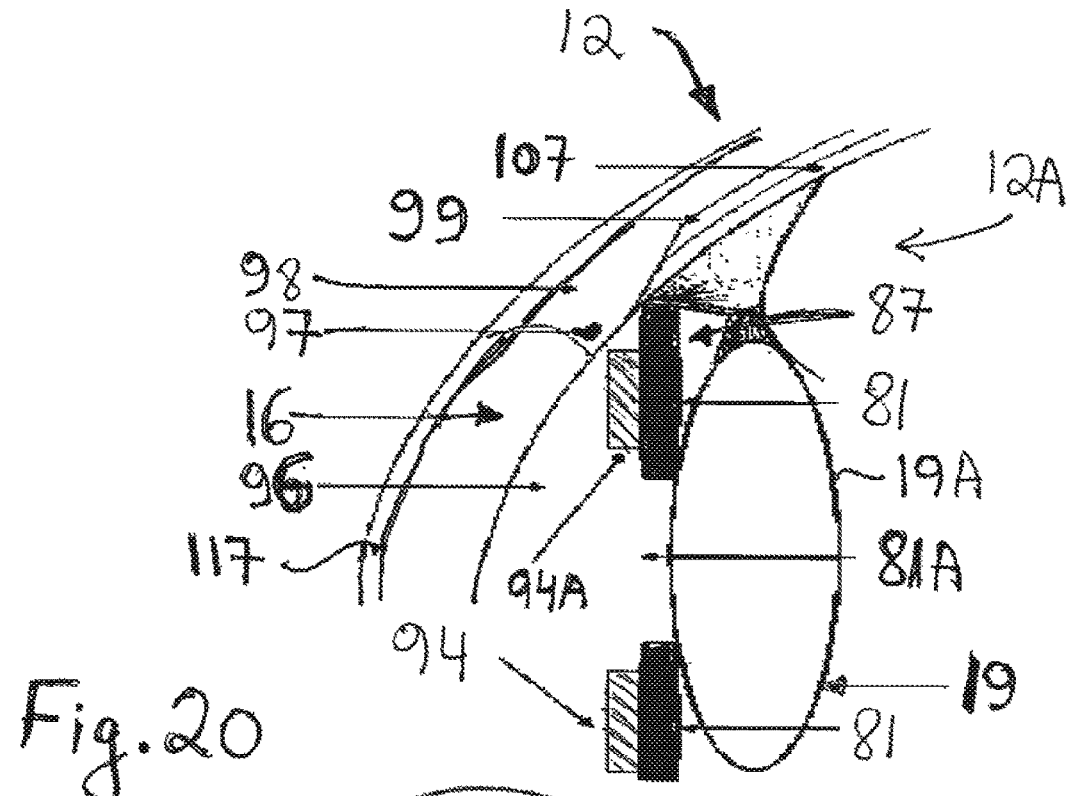
FIG. 20 is a schematic cross-sectional view illustrating a part of an eye and the position of an inductive coil placed in the anterior chamber of the eye, in accordance with some embodiments of the systems of the present application.

Reference is now made to FIG. 20 which is a schematic cross-sectional view illustrating a part of an eye and the position of an inductive coil placed in the anterior chamber of the eye, in accordance with some embodiments of the systems of the present application. The eye 12 has a vitreous body 12A, a lens 19, a cornea 16, and an iris 81 having a pupil 81A therein. The anterior chamber 96, the choroid 107, the supra-choroidal space 99, the sclera 98, the conjunctiva 117 and schlemm's canal 97 of the eye 12 are also illustrated in FIG. 20. In accordance with some embodiments of the systems of the present application, a coil 94 may be placed between the iris 81 and the cornea 16 within the anterior chamber 96 of the eye 12. The coil 94 has an opening 94A therein This placement allows light entering the eye 12 to pass and enter the pupil 81A of the iris 81 It is noted that the upper eyelid of the eye 12 and the permanent magnet implanted in the upper eyelid are not shown in FIG. 20 for the sake of clarity of illustration. The (optional) current rectifier, the (optional) charge storage device of the electric power providing system are not shown in FIG. 20, but may be disposed on the coil 94, or may be disposed in other parts of the eye and suitably electrically coupled to the coil 94 as disclosed in detail hereinabove. A medical device or medical implant (not shown in FIG. 20) may be suitably electrically coupled to the coil 94 and/or to any optional current rectifier and/or charge storage device included in the system, as disclosed in detail hereinabove.

It is noted that the placement and/or position and/or orientation of the inductors of the systems of the present application are not limited to those disclosed hereinabove and illustrated in the drawing figures. Rather, in accordance with some embodiments, such inductor(s) (for example, coils) may be placed in front of the iris 81 (in the anterior chamber 96), between the iris 81 and the lens 19 (within the posterior chamber 87), behind the lens 19, attached to the rear surface 19A of the lens 19, anywhere within the vitreous body 12A of the eye 12, or implanted in or under the conjunctiva 117 or in the sclera 98 of the eye 12.

It is further noted that the systems of the present application are not limited to embodiments including a single coil (or inductor) and/or a single permanent magnet.

Figure 21:
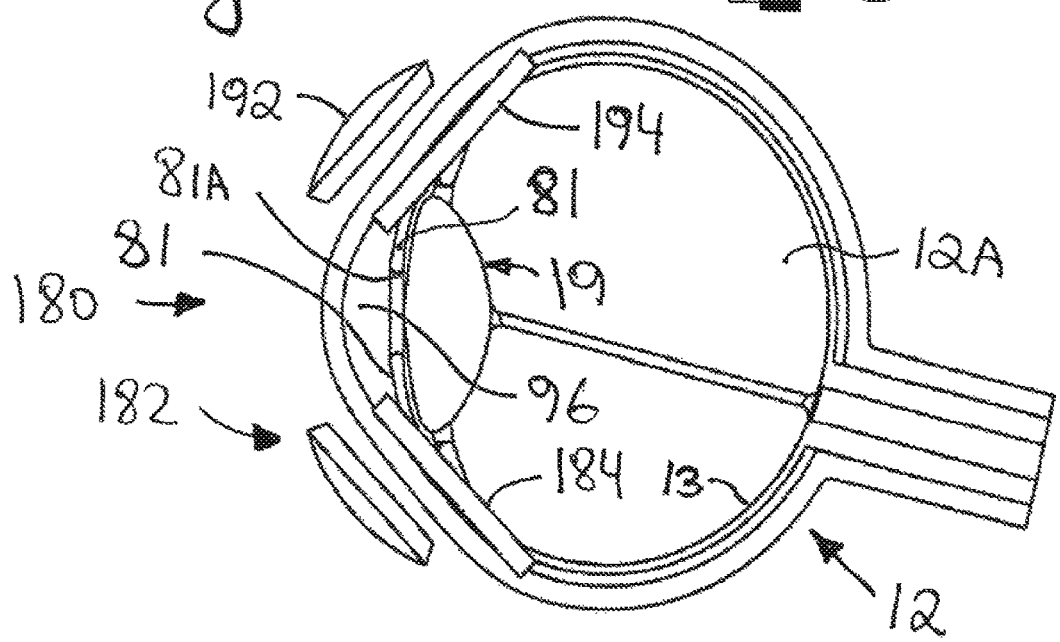
FIG. 21 is a schematic cross-sectional view, illustrating part of a system having two inductors and two permanent magnets for providing electrical energy to an ocular implant or to device implanted in the eye, in accordance with some embodiments of the systems of the present application.

Reference is now made to FIG. 21, which is a schematic cross-sectional view, illustrating part of a system having two inductors and two permanent magnets for providing electrical energy to an ocular implant or to device implanted in the eye, in accordance with some embodiments of the systems of the present application.

The system 180 includes two induction coils 184 and 194 and two corresponding permanent magnets 182 and 192. The coils 184 and 194 may be implanted in the anterior chamber 96 of the eye 12 as illustrated. The permanent magnet 192 may be implanted in the upper eyelid of the eye 12 (the upper eyelid is not shown for the sake of clarity of illustration) and the permanent magnet 182 may be implanted in the lower eyelid of the eye 12 (the upper eyelid is not shown for the sake of clarity of illustration). The coils 184 and 194 may be electrically coupled to suitable (optional) current rectifiers (not shown) and/or to (optional) charge storage device(s), as disclosed hereinabove. The coils 184 and 194 may each provide power to a separate device disposed within the eye. Alternatively, in accordance with some embodiments of the system, the coils 184 and 194 may electrically charge the same (optional) charge storage device through suitable current rectifiers (not shown).

The magnet 192 may be moved by blinking of the upper eyelid as disclosed in detail hereinabove for the permanent magnet 22 of the system 20 (of FIG. 2) hereinabove. While the movements of the lower eyelid may be much smaller in amplitude than the movements of upper eyelid, the induction of currents in the coil 184 (and in the coil 194) may be caused be voluntary or involuntary (such as saccadic movements) movements of the eye 12. It is noted that the medical device(s) powered by the system 180 are not shown in FIG. 21 for the sake of clarity of illustration but may be any of the types of devices disclosed in the present application.

Figure 22:
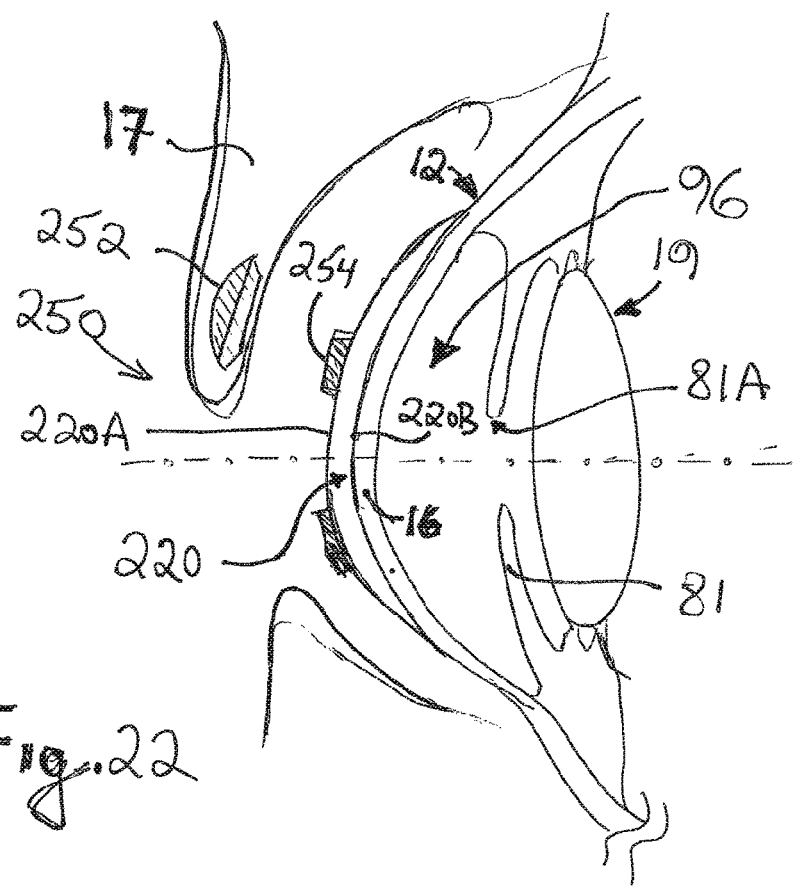
FIG. 22 is a schematic cross-sectional view of a system for providing electrical power to a device included in a contact lens attached to the eye.
Figure 23:
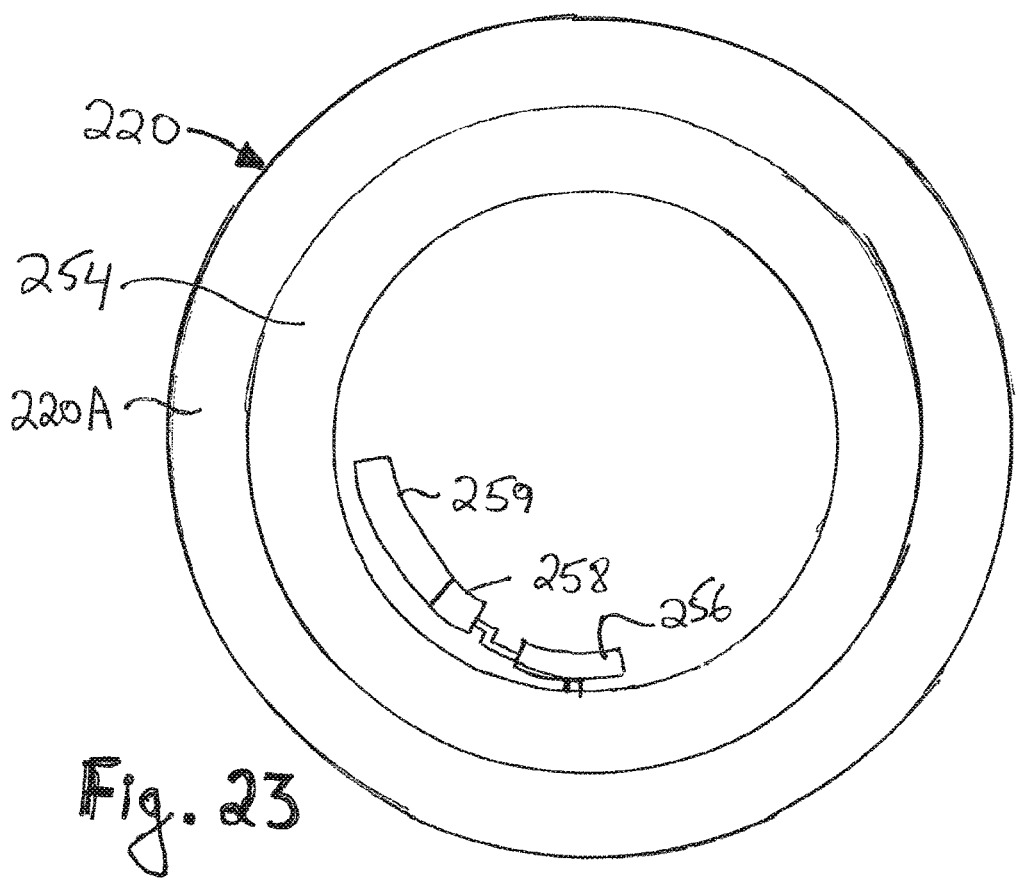
FIG. 23 is a schematic front view of the contact lens of FIG. 22.

Reference is now made to FIGS. 22-23. FIG. 22 is a schematic cross-sectional view of a system for providing electrical power to a device included in a contact lens attached to the eye. FIG. 23 is a schematic front view of the contact lens of FIG. 22.

The system 250 may include a permanent magnet 252 implanted in or attached to the upper eyelid 17, the system 250 also includes a contact lens 220 Which may be attached to the eye 12 by placement on the cornea 16. The contact lens 220 may be any suitable type of transparent contact lens and may have vision correcting optical properties required to correct a visual impairment. In some embodiments of the system the contact lens 220 may also be a transparent lens shaped to have no optical correcting properties (if the user does not have a visual impairment to be corrected).

Turning to FIG. 23, the contact lens 220 includes a circularly shaped induction coil 254. The induction coil 254 may be attached to the surface 220A of the contact lens 220 by a suitable adhesive or, alternatively may be printed on the surface 220A. In other embodiments of the system, the coil 254 may be partially or fully embedded in the material forming the contact lens 220. The contact lens 220 also includes a current rectifier 256, suitably coupled to the induction coil 254. In some embodiments, the rectifier 256 may be a suitable microminiaturized integrated circuit (IC) suitably attached or glued to the surface 220A or, alternatively partially or fully embedded within the material forming the contact lens 220.

The contact lens 220 also may also include an (optional) charge storage device 258 (such as, for example a suitably miniaturized electrochemical rechargeable cell, or a supercapacitor), suitably electrically coupled to the current rectifier 256 for storing charge therein as disclosed in detail hereinabove. The contact lens 220 also includes a medical device 259 electrically coupled to the charge storage device 258 and/or to the current rectifier 256. The medical device 259 may be suitably attached or glued to the surface 220A of the contact lens but in some embodiments may be fully or partially embedded in the material forming the lens 220. Alternatively, the medical device 259 may be attached to or glued to the surface 220B of the contact lens 220, such that at least part of the medical device 259 may have access to part of the surface of the cornea 16 and/or to the fluid wetting the cornea 16. The medical device 259 may be any suitable type of medical device. For example, the medical device 259 may be a sensing device for determining the intraocular pressure (for glaucoma patients or for patients at risk of developing glaucoma). In such an exemplary embodiment, the device 259 may monitor intraocular pressure and may store and/or wirelessly transmit data indicative to the intraocular pressure to an external receiver (not shown). Depending on the particular application and on the specific type of the medical device 259, the device 259 may include optical sensors, chemical sensors, pressure sensors or any other suitable type of sensor, and may also include any suitable electronic circuitry for controlling the operation of the device, performing computations, storing data and/or transmitting data to an external wireless receiver. The device 259 may also be configured to release a substance into the fluid bathing the eye in a controlled manner.

In operation of the system 250, after the magnet 252 is implanted in or attached to the upper eyelid 17, the contact lens 220 may be inserted into the eye 12 and placed in contact with the surface of the cornea 16. Blinking of the upper eyelid 17 as well as various eye movements may result in changes in the magnetic flux within the coil 254 as disclosed in detail hereinabove for other embodiments of the systems. The alternating (e.g., pulsed) currents flowing through the coil 254 may be rectified by the rectifier 256 and may be stored by the charge storage device 258 and may be fed to the medical device 259.

It is noted that while the inductors of the systems disclosed in the present application may be coils having a generally circular or spiral shapes, this is not obligatory. Rather, the inductors of the systems of the present application may be any suitable type of inductors, such as, for example, non-circularly shaped inductors, elliptically shaped coils, polygonal shaped coils, single layer coils, multiple layered coils or any other suitable type of coils or inductors. The parameters of such inductors, such as, for example the inductance, number of coil windings, number of layers, the dimensions and shapes of the coils, the electrical resistance of the coil windings and other electrical and physical parameters of the coil(s) may depend, inter alia, on the location and/or position and/or distance of the coil(s) relative to the permanent magnet(s) of the system, the shape and magnetic properties of the permanents magnet(s), the dimensions of any substrate to which the coil(s) are attached or within which the coil(s) are embedded (for embodiments in which the coil(s) are attached to or embedded in a substrate), the dimensions of the body part or organ in which the inductor(s) are disposed, and other mechanical and electrical considerations.

It will be appreciated that while the examples hereinabove disclose systems, methods, devices and kits based on permanent magnet(s) that induce electrical currents in inductors responsive to movements of the magnets and/or coils relative to each other, other embodiments may be based on magnetic interaction between a permanent magnet implanted in or attached to a first body part and another magnet or ferromagnetic member that is attached to or implanted in a second body part.

For example, a system may include a permanent magnet (such as, for example the permanent magnet 22 of FIG. 2 or the magnet 82 of FIG. 5) implanted in the upper lid 17. Instead of a coil or inductor, the system may include another permanent magnet (not shown) or a ferromagnetic member (not shown) that is implanted within the eye 12. When the first permanent magnet to moves with the upper lid 17 during blinking, the magnetic coupling between the first magnet and the second magnet (or between the first permanent magnet and the ferromagnetic member) may result in a force acting on the second permanent magnet or on the ferromagnetic member to cause a movement of the second permanent magnet or of the ferromagnetic member.

Such a force may be used to produce energy for a device implanted in the eye. For example, in some embodiments, the mechanical movement of the second permanent magnet (or ferromagnetic member) may be applied to a piezoelectric material mechanically coupled to the second permanent magnet or ferromagnetic member to generate electrical currents which may be supplied to the implanted device (possibly after conditioning that may include rectification).

In some embodiments, the mechanical force or movement of the second permanent magnet or of the ferromagnetic member may be applied to a part of the implanted device by mechanical coupling of the second permanent magnet (or the ferromagnetic member) to a mechanical (movable) part of the implanted device (such as for example, a mechanical pump, a flywheel, a movable lever a movable crankshaft, a compressible spring or any other suitable movable part). The movement of the second permanent magnet or the ferromagnetic member may thus provide mechanical energy to the device implanted in the eye.

It is noted that such systems with magneto-mechanical coupling are not limited to use only in the eye but may also be used in any body parts described herein by suitable adaptation of the system to the body parts in which the system parts are to be implanted or attached.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Citation or identification of any reference in this application shall not be construed as an admission that such reference is available as prior art to the present invention. To the extent that section headings are used, they should not be construed as necessarily limiting.

What is claimed is:

1. An energy harvesting apparatus for harvesting energy from relative motion of an eyeball and an eyelid to drive an electrical device, the energy harvesting apparatus, comprising:
   (a) a coil of conductive wire;
   (b) a support arrangement for supporting said coil in or on an eyeball;
   (c) a permanent magnet configured for deployment in or on an eyelid, said permanent magnet generating a magnetic field oriented to generate a variation of magnetic flux through said coil on blinking motion of the eyelid; and
   (d) rectifying circuitry electrically connected across said coil and configured to rectify an electrical output of said coil to generate a DC output for driving the electrical device,
   wherein said permanent magnet is implemented as a compound permanent magnet having a plurality of different regions of magnetization, said regions of magnetization having differing directions of magnetization so as to generate magnetic field shaping with enhanced flux intensity along an inwards-facing direction from said compound permanent magnet.

2. The apparatus of claim 1, further comprising an electrical storage component electrically connected to said rectifying circuitry for storing energy from the DC output for driving the electrical device.

3. The apparatus of claim 1, wherein said support arrangement is configured to be applied to an external surface of the eyeball.

4. The apparatus of claim 1, wherein said support arrangement is integrated with a contact lens configured to be applied to an external surface of the eyeball.

5. The apparatus of claim 1, wherein said support arrangement is configured to be deployed intraocularly.

6. The apparatus of claim 1, wherein said support arrangement is integrated with an intraocular lens.

7. The apparatus of claim 1, wherein said support arrangement is configured to support said coil with said coil encircling an optic axis of the eyeball.

8. An energy harvesting apparatus for harvesting energy form relative motion of an eyeball and an eyelid to drive an electrical device, the energy harvesting apparatus, comprising:
   (a) a coil of conductive wire;
   (b) a support arrangement for supporting said coil in or on an eyeball;
   (c) a soft magnetic core mechanically associated with, and deployed within, said coil;
   (d) a permanent magnet configured for deployment in or on an eyelid, said permanent magnet generating a magnetic field oriented to generate a variation of magnetic flux through said coil on blinking motion of the eyelid; and
   (e) rectifying circuitry electrically connected across said coil and configured to rectify an electrical output of said coil to generate a DC output for driving the electrical device.

9. The apparatus of claim 1, wherein said permanent magnet is formed as a flat or curved slab contiguous in two major dimensions, and having a maximum local thickness, each of said two major dimensions being at least five times greater than said maximum local thickness.

10. The apparatus of claim 9, wherein a direction of magnetization of at least part of said permanent magnet is substantially perpendicular to both of said two major dimensions.

11. The apparatus of claim 1, wherein said permanent magnet is formed as a slab having a concave major surface for accommodating a curvature of the eyeball, and a convex major surface.

12. The apparatus of claim 1, further comprising a shield of soft-magnetic material deployed on an outward-facing surface of said permanent magnet.

13. The apparatus of claim 1, further comprising an adhesive pad associated with said permanent magnet for attaching said permanent magnet to a surface of the eyelid.

14. The apparatus of claim 1, wherein said permanent magnet is encased in a non-magnetic layer of biocompatible material for implantation into the eyelid.

15. The apparatus of claim 2, further comprising voltage boosting circuitry electrically associated with said coil or said rectifying circuitry and configured to boost a voltage of the output reaching said electrical storage component.

16. An energy harvesting apparatus for harvesting energy from relative motion of an eyeball and an eyelid to drive an electrical device, the energy harvesting apparatus, comprising:
   (a) a coil of conductive wire deployed in or on the eyeball;
   (b) a permanent magnet deployed in or on the eyelid, said permanent magnet generating a magnetic field oriented to generate a variation of magnetic flux through said coil on blinking motion of the eyelid; and
   (c) rectifying circuitry electrically connected across said coil and configured to rectify an electrical output of said coil to generate a DC output for driving the electrical device,
   wherein said permanent magnet is implemented as a compound permanent magnet having a plurality of different regions of magnetization, said regions of magnetization having differing directions of magnetization so as to generate magnetic field shaping with enhanced flux intensity along an inwards-facing direction from said compound permanent magnet.

17. The apparatus of claim 16, wherein said coil is integrated with a contact lens applied to an external surface of the eyeball.

18. The apparatus of claim 16, wherein said coil is deployed in or under the conjunctiva or the sclera of the eyeball.

19. The apparatus of claim 16, wherein said coil is deployed in, or attached to, the cornea of the eyeball.

20. The apparatus of claim 16, wherein said coil is deployed within the vitreous body, the anterior chamber, the sulcus, the capsular bag or the posterior chamber of the eyeball, or is integrated with an intraocular lens.

* * * * *